(12) United States Patent
Ueda

(10) Patent No.: US 10,722,264 B2
(45) Date of Patent: Jul. 28, 2020

(54) MEDICAL PUNCTURE NEEDLE AND METHOD FOR MANUFACTURING PUNCTURE NEEDLE

(71) Applicant: Terumo Kabushiki Kaisha, Tokyo (JP)

(72) Inventor: Takehiko Ueda, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 130 days.

(21) Appl. No.: 15/883,638

(22) Filed: Jan. 30, 2018

(65) Prior Publication Data

US 2018/0153579 A1 Jun. 7, 2018

Related U.S. Application Data

(63) Continuation of application No. PCT/JP2016/003399, filed on Jul. 20, 2016.

(30) Foreign Application Priority Data

Jul. 30, 2015 (JP) .................................. 2015-151313

(51) Int. Cl.
*A61B 17/34* (2006.01)
*A61M 5/158* (2006.01)
(Continued)

(52) U.S. Cl.
CPC .......... *A61B 17/3421* (2013.01); *A61M 5/158* (2013.01); *A61M 5/32* (2013.01);
(Continued)

(58) Field of Classification Search
CPC ..................... A61M 5/3286; A61M 2205/195
See application file for complete search history.

(56) References Cited

U.S. PATENT DOCUMENTS 3,308,822 A * 3/1967 De Luca ............. A61M 5/3286
604/274
3,448,740 A * 6/1969 Figge .................. A61M 5/3286
604/274

(Continued)

FOREIGN PATENT DOCUMENTS

| CN | 1140092 A | 1/1997 |
| CN | 103237568 A | 8/2013 |

(Continued)

OTHER PUBLICATIONS

International Search Report issued in International Patent Application No. PCT/JP2016/003399 dated Sep. 6, 2016.
(Continued)

*Primary Examiner* — Jenna Zhang
(74) *Attorney, Agent, or Firm* — Foley & Lardner LLP

(57) ABSTRACT

A medical puncture needle includes: a distal end portion including a needle point; and a rod-like main body portion continuous with the distal end portion. The distal end portion includes a blade surface. The blade surface includes: a first blade surface portion on a front side of the distal end portion, the first blade surface portion being inclined with respect to a center axis of the main body portion and extending to the needle point, and a second blade surface portion on a back side of the distal end portion. When a virtual plane including the center axis of the main body portion is established, the second blade surface portion comprises a curved surface in which an angle with respect to the virtual plane in a cross section orthogonal to the center axis direction gradually increases toward the needle point side in the center axis direction.

7 Claims, 11 Drawing Sheets

(51) Int. Cl.
- *B21G 1/08* (2006.01)
- *A61M 5/32* (2006.01)
- *B24B 19/16* (2006.01)
- *A61B 17/06* (2006.01)
- *A61B 17/00* (2006.01)
- *A61M 25/06* (2006.01)

(52) U.S. Cl.
CPC ............ *A61M 5/3286* (2013.01); *B21G 1/08* (2013.01); *B24B 19/16* (2013.01); *A61B 2017/00526* (2013.01); *A61B 2017/061* (2013.01); *A61B 2017/06071* (2013.01); *A61B 2017/3454* (2013.01); *A61M 25/0606* (2013.01)

(56) References Cited

U.S. PATENT DOCUMENTS

| | | | | |
|---|---|---|---|---|
| 5,752,942 | A | * | 5/1998 | Doyle ............ B24B 19/16 604/274 |
| 2005/0107751 | A1 | * | 5/2005 | Yatabe ............ A61M 5/158 604/272 |

FOREIGN PATENT DOCUMENTS

| | | |
|---|---|---|
| CN | 107921203 A | 4/2018 |
| JP | 2008-154843 A | 7/2008 |
| JP | 2008-528222 A | 7/2008 |
| JP | 2012-115336 A | 6/2012 |
| JP | 2014-004249 A | 1/2014 |

OTHER PUBLICATIONS

Office Action and Search Report dated Mar. 5, 2020 in corresponding Chinese Patent Application No. 2016800445017.

\* cited by examiner

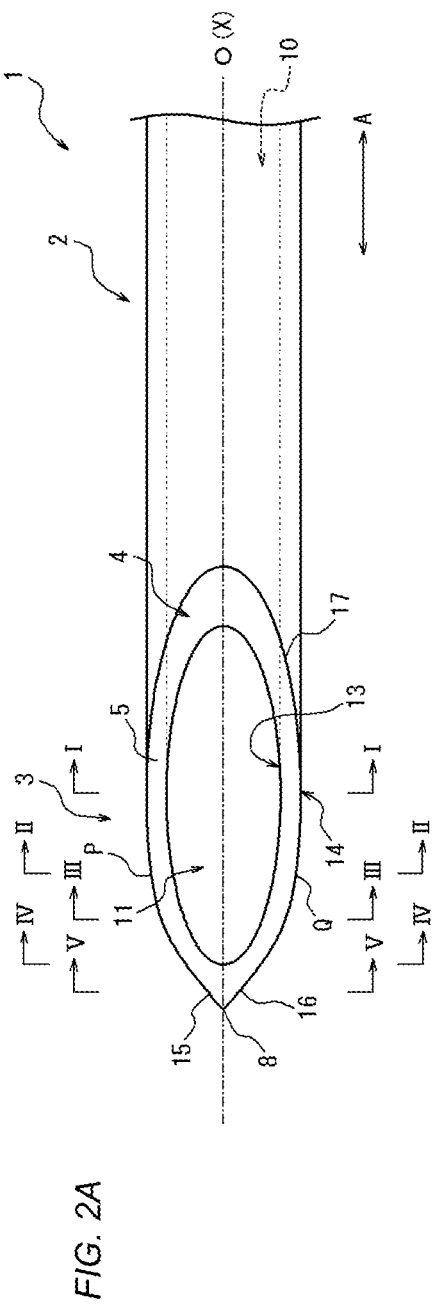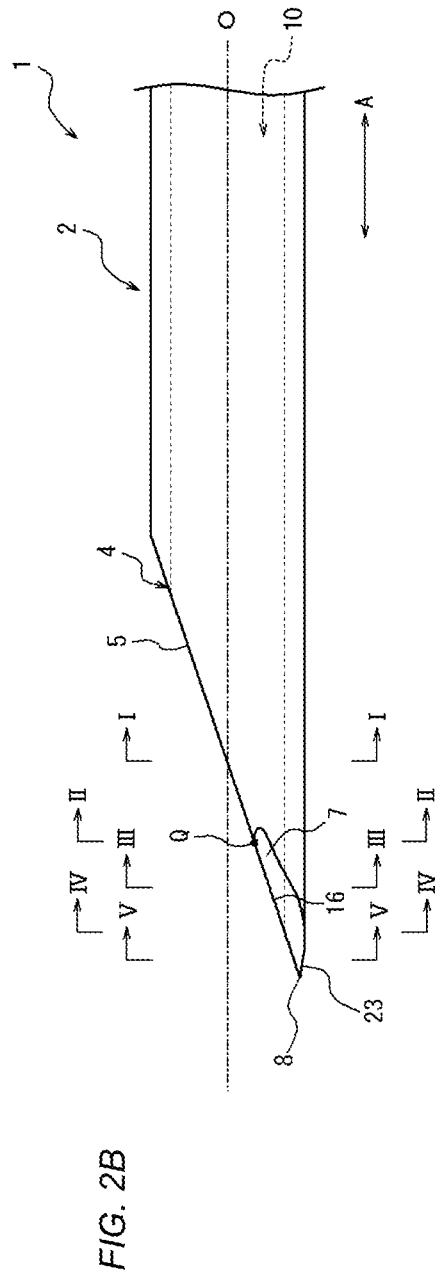
FIG. 2A
FIG. 2B

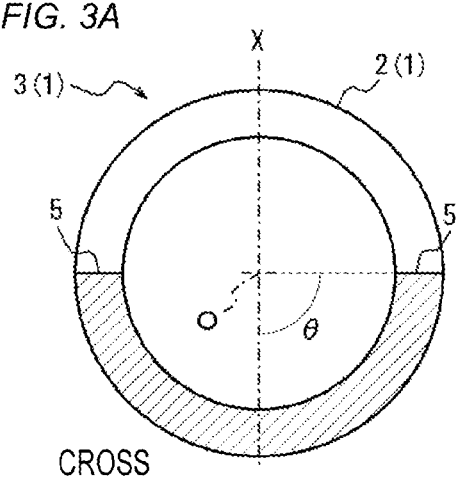
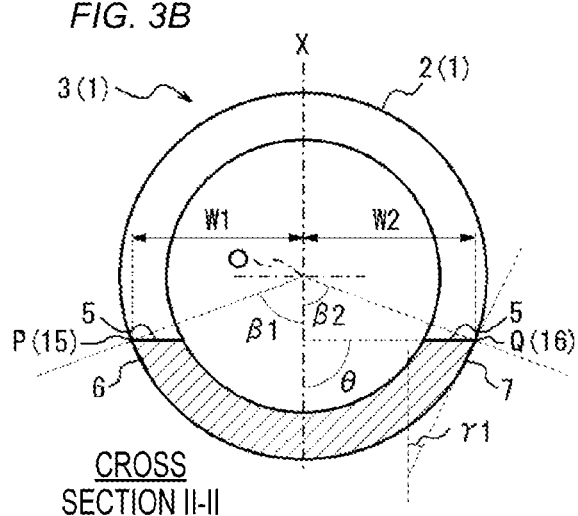
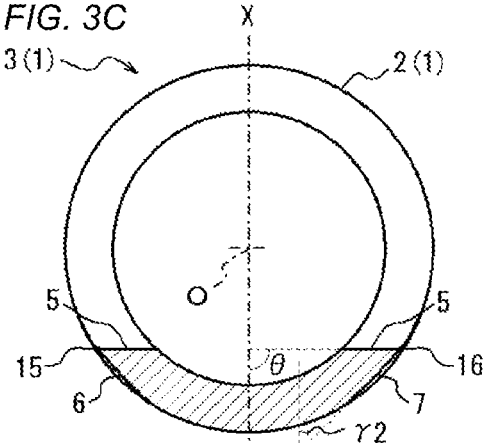
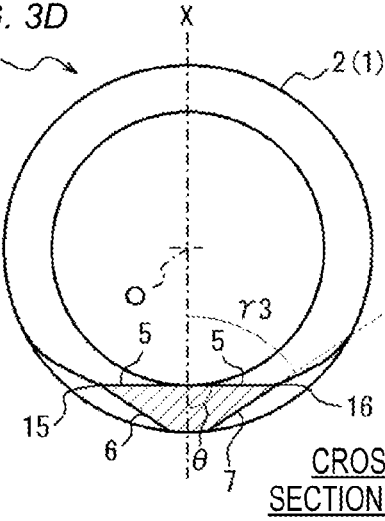
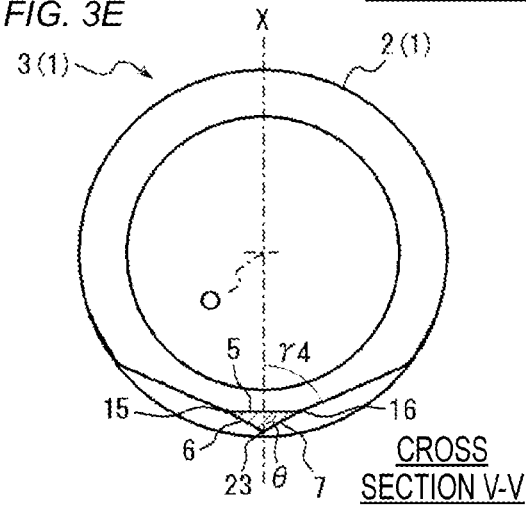

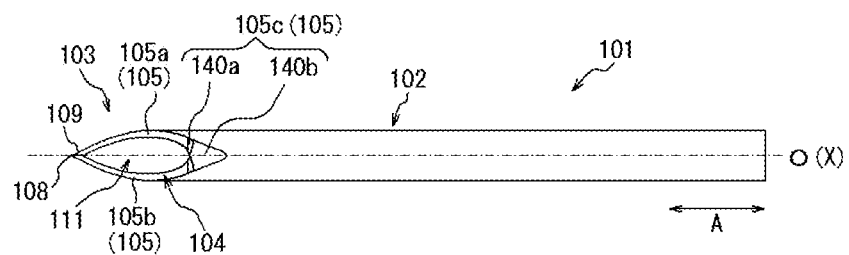
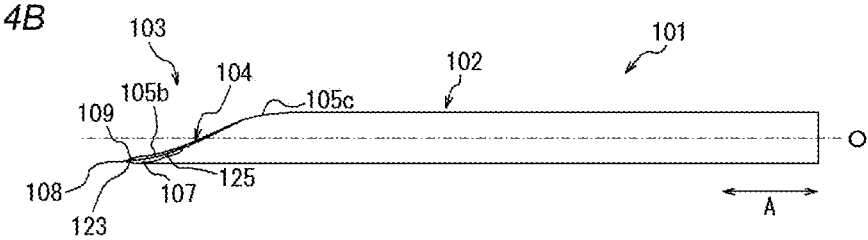
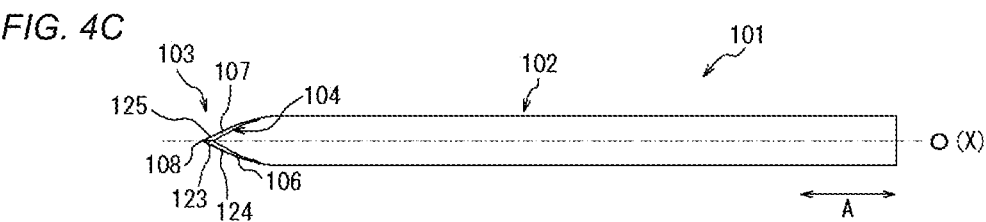
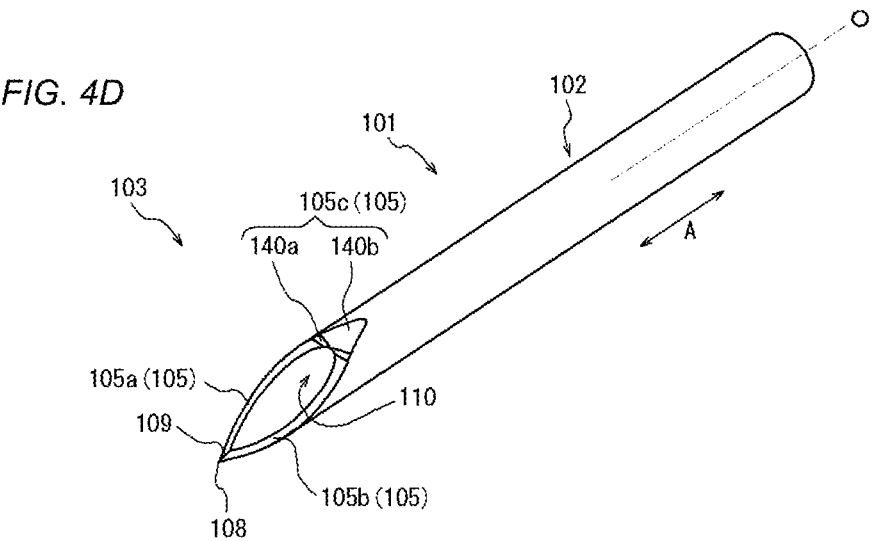

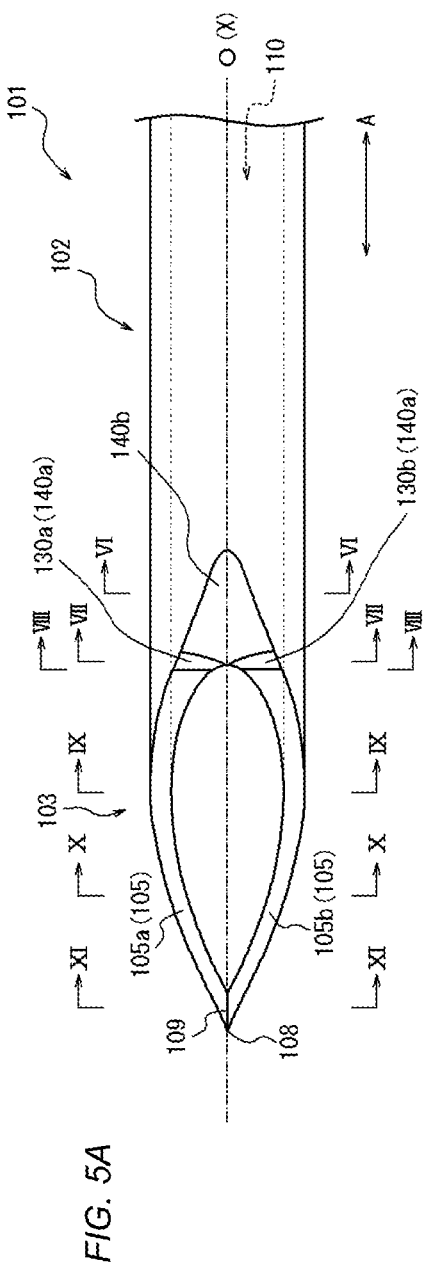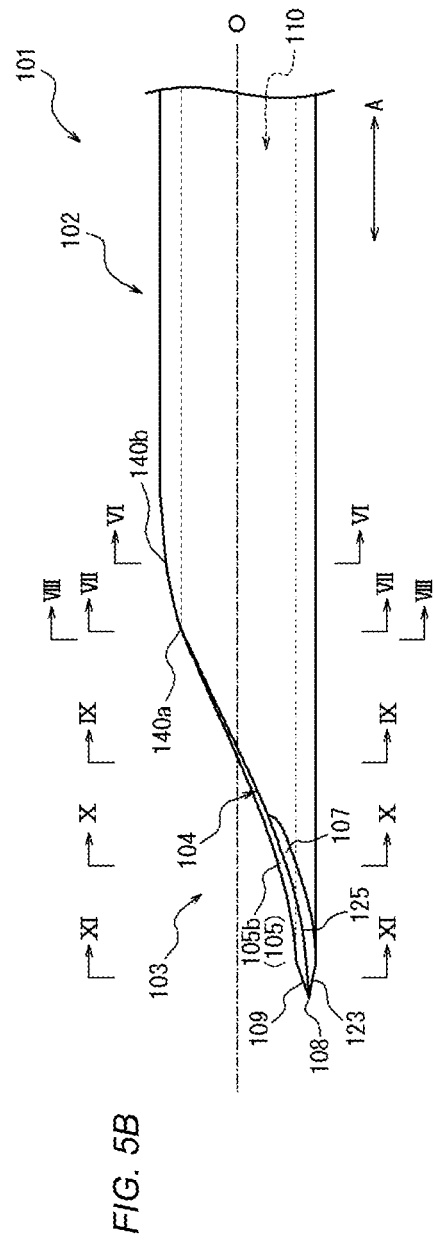

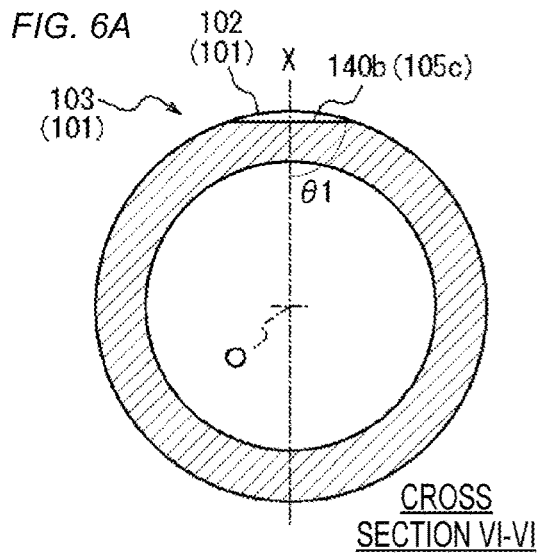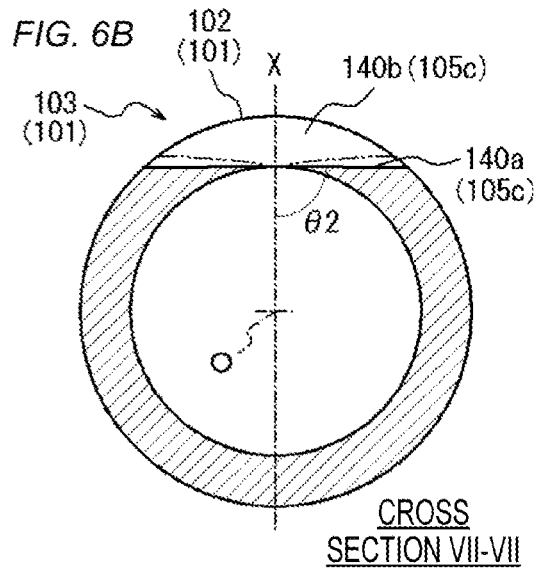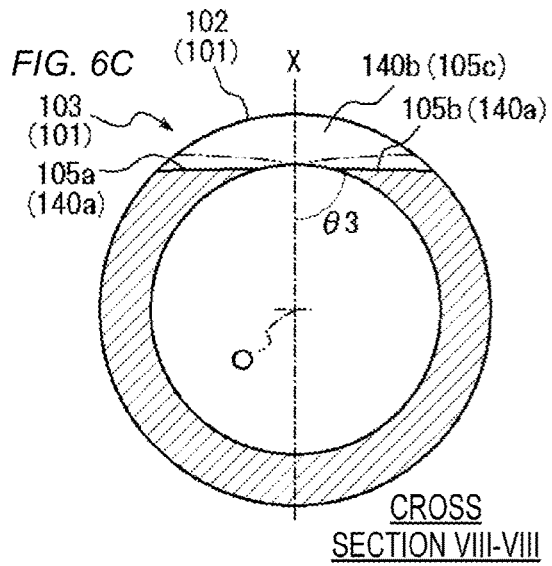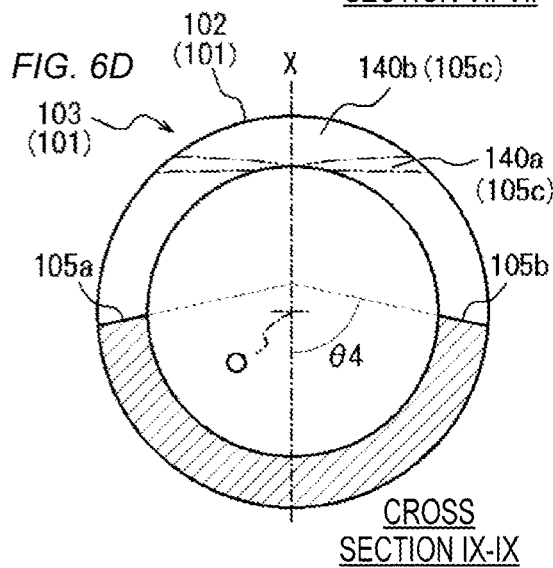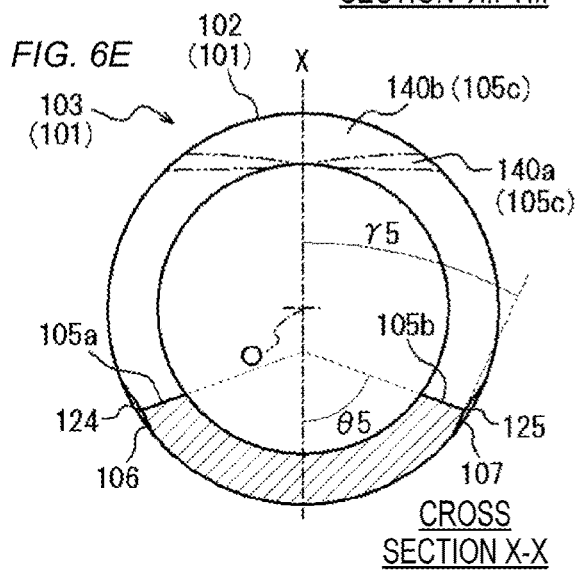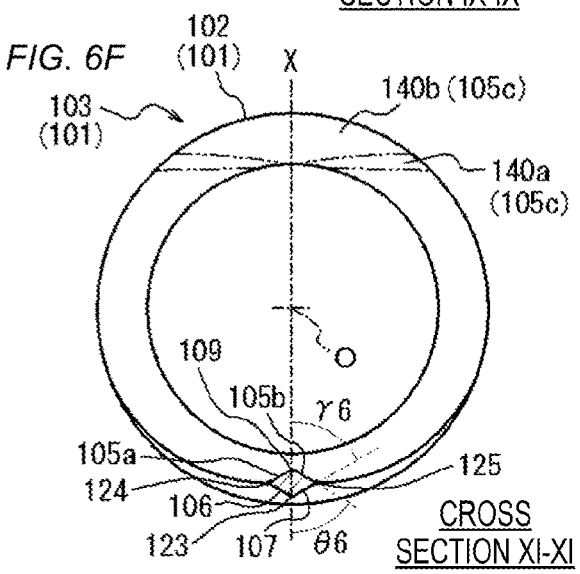

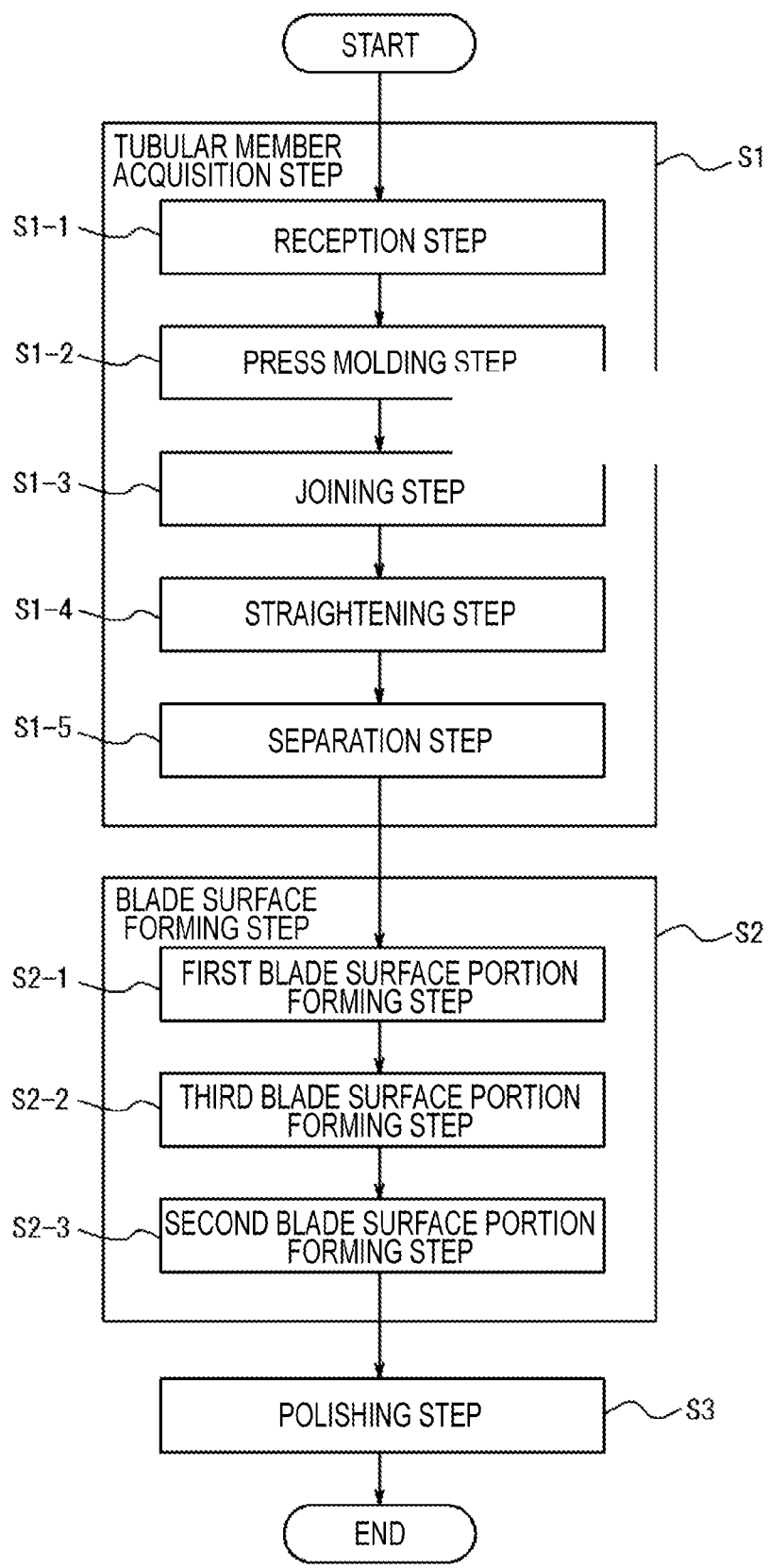

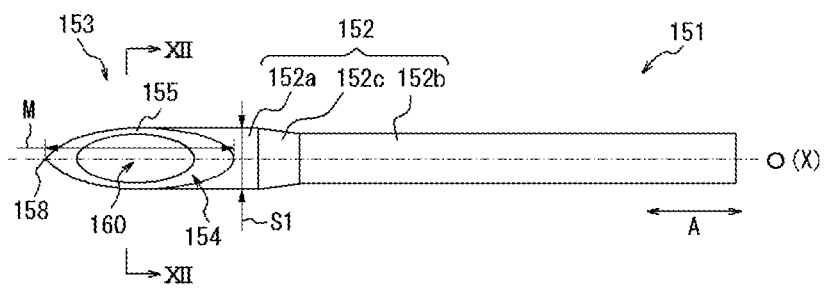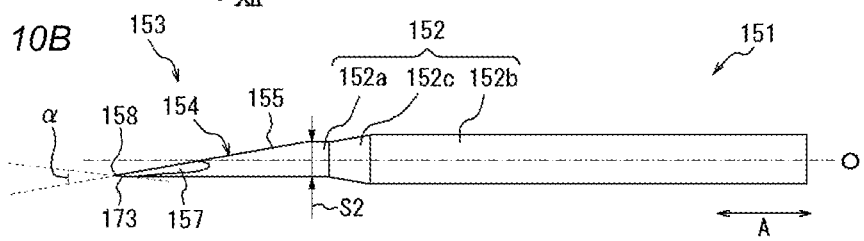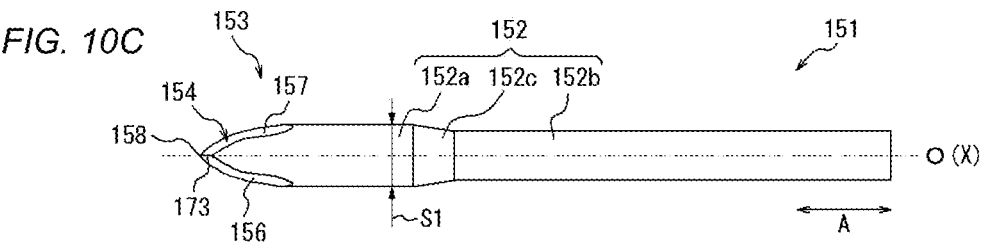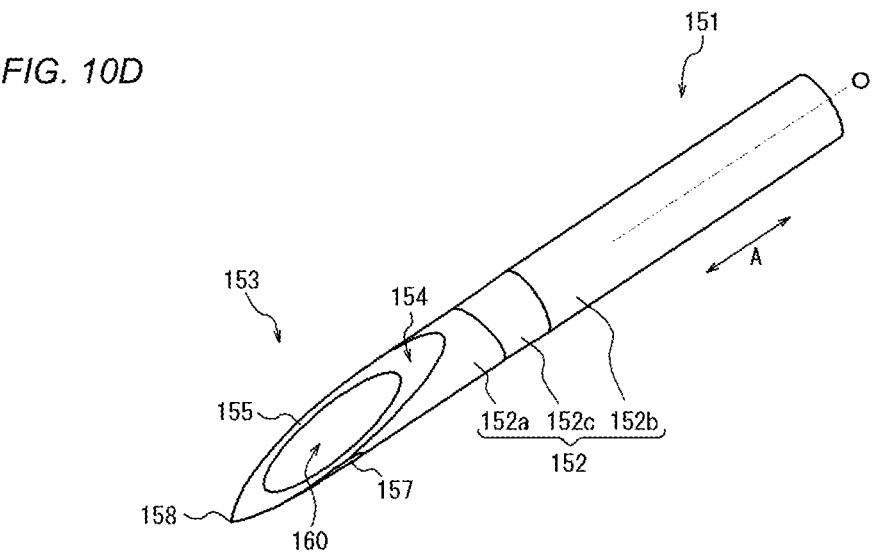

CROSS SECTION XII-XII

MEDICAL PUNCTURE NEEDLE AND METHOD FOR MANUFACTURING PUNCTURE NEEDLE

CROSS-REFERENCE TO RELATED APPLICATIONS

The present application is a bypass continuation of PCT Application No. PCT/JP2016/003399, filed on Jul. 20, 2016, which claims priority to Japanese Application No. 2015-151313, filed on Jul. 30, 2015, the contents of which are hereby incorporated by reference in their entireties.

BACKGROUND

The present disclosure relates to a medical puncture needle and a method for manufacturing the puncture needle.

Conventionally, there is a known medical puncture needle such as a blood collection needle or an indwelling needle for infusion, which includes, at a distal end portion, a blade surface inclined with respect to the longitudinal direction of the puncture needle in order to alleviate pain when puncturing the human body with the puncture needle.

JP 2014-004249 A discloses a puncture needle of this type having a blade surface shape called a "back-cut bevel point" (hereinafter referred to simply as "back-cut type"). A puncture needle having a back-cut type blade surface disclosed in JP 2014-004249 A is superior in rectilinearity, and thus, is used to puncture a target site at a relatively deep position in the body from the body surface such as puncture into an artery or puncture into a central vein.

SUMMARY

Meanwhile, the puncture needle having a back-cut type blade surface disclosed in JP 2014-004249 A has a flat-cut surface as a blade surface portion on the front side and a planar back-cut surface as a blade surface portion on the back side, in which the flat-cut surface and the back-cut surface intersect with each other at a ridgeline to form a linear cutting edge as a blade edge having a needle point at one end of the ridgeline. Therefore, when puncturing with the puncture needle disclosed in JP 2014-004249 A, this blade edge acts to incise the skin, making it possible to reduce penetration resistance, and alleviate the pain sensed by the patient, or the like.

However, reducing the thickness of the puncture needle decreases the planar back-cut surface, making it difficult to provide a cutting edge with a length sufficient to incise the skin. Therefore, while the skin can be incised by the cutting edge as a blade edge in the vicinity of the needle point, when the proximal end of the cutting edge on the side opposite to the needle point passes through the skin, the outer surface of the puncture needle is inserted to forcibly push the incision apart, causing the patient pain.

In view of the above-described problem, it is an object of certain embodiments of the present disclosure to provide a puncture needle having a back-cut type blade surface capable of easily obtaining the length of the blade edge and a method for manufacturing the puncture needle.

According to one embodiment, a medical puncture needle includes: a distal end portion including a needle point; and a rod-like main body portion continuous with the distal end portion, in which the distal end portion includes a blade surface, the blade surface includes a first blade surface portion inclined with respect to a center axis of the main body portion and extending to the needle point and includes a second blade surface portion formed on a back side of the first blade surface portion, and in a case where one virtual plane including the center axis of the main body portion is established, the second blade surface portion is constituted with a curved surface in which an angle with respect to the virtual plane in a cross section orthogonal to the center axis direction gradually increases toward the needle point side in the center axis direction.

In one aspect, the blade surface includes a third blade surface portion formed on the back side of the first blade surface portion, and the second blade surface portion and the third blade surface portion intersect each other to be a ridgeline and form a blade edge having the needle point as one end by the ridgeline on the back side of the first blade surface portion.

In one aspect, the third blade surface portion is constituted with a curved surface in which an angle with respect to the virtual plane in a cross section orthogonal to the center axis direction gradually increases toward the needle point side in the center axis direction.

In one aspect, the virtual plane can be established in one plane perpendicular to the first blade surface portion and including the center axis.

According to another embodiment, a medical puncture needle includes: a distal end portion including a needle point; and a rod-like main body portion continuous with the distal end portion, in which the distal end portion includes a blade surface, the blade surface includes: a first blade surface portion inclined with respect to a center axis of the main body portion and extending to the needle point; a second blade surface portion formed on a back side of the first blade surface portion; and a third blade surface portion formed on the back side of the first blade surface portion, the second blade surface portion and the third blade surface portion intersect each other to be a ridgeline and form a blade edge having the needle point as one end by the ridgeline on the back side of the first blade surface portion, and in a case where the blade edge is defined as a first blade edge, the first blade surface portion and the second blade surface portion intersect each other to be a ridgeline and form a second blade edge having the needle point as one end by the ridgeline while the first blade surface portion and the third blade surface portion intersect each other to be a ridgeline and form a third blade edge having the needle point as one end by the ridgeline, and each of the second blade edge and the third blade edge is formed with a curved line.

In one aspect, the outer edge of the first blade surface portion is constituted with the second blade edge, the third blade edge, and a protruding curved line-shaped main body portion side outer edge portion connecting one end of the second blade edge on the main body portion side with one end of the third blade edge on the main body portion side, and the second blade edge and the third blade edge are connected to the main body portion side outer edge portion by a continuous curved line without passing through an apex.

In another embodiment, a method for manufacturing a medical puncture needle is a method of forming a blade surface on one end portion of a rod-like member by bringing the one end portion into sliding contact with a grinding surface of a rotating grindstone, the method for manufacturing a medical puncture needle including forming a blade surface portion constituted with a curved surface by bringing the one end portion into sliding contact with the grinding surface while varying a tilt angle of a center axis with respect to the grinding surface while causing the rod-like member to pivot about the center axis of the rod-like member.

According to certain embodiments of the present disclosure, it is possible to provide a puncture needle having a back-cut type blade surface capable of easily obtaining the length of the blade edge and a method for manufacturing the puncture needle.

BRIEF DESCRIPTION OF THE DRAWINGS

FIGS. 1A-1D are diagrams illustrating a puncture needle according to an embodiment of the present invention, in which FIG. 1A is a plan view of a front side, FIG. 1B is a side view, FIG. 1C is a plan view of a back side, and FIG. 1D is a perspective view.

FIG. 2A is an enlarged view of a distal end portion illustrated in FIG. 1A, and FIG. 2B is an enlarged view of a distal end portion illustrated in FIG. 1B.

FIG. 3A is a cross sectional view taken along line I-I in FIGS. 2A and 2B, FIG. 3B is a cross sectional view taken along line II-II in FIGS. 2A and 2B, FIG. 3C is a cross sectional view taken along line III-III in FIGS. 2A and 2B, FIG. 3D is a cross sectional view taken along line IV-IV in FIGS. 2A and 2B, and FIG. 3E is a cross sectional view taken along line V-V in FIGS. 2A and 2B.

FIGS. 4A-4D are diagrams illustrating a puncture needle different from the puncture needle illustrated in FIGS. 1A-1D, in which FIG. 4A is a plan view of a front side, FIG. 4B is a side view, FIG. 4C is a plan view of a back side, and FIG. 4D is a perspective view.

FIG. 5A is an enlarged view of a distal end portion illustrated in FIG. 4A, and FIG. 5B is an enlarged view of a distal end portion illustrated in FIG. 4B.

FIGS. 6A, 6B, 6C, 6D, 6E, and 6F are cross sectional views taken along lines VI-VI, VII-VII, VIII-VIII, IX-IX, X-X, and XI-XI in FIGS. 5A and 5B, respectively.

FIGS. 7A-7D are diagrams illustrating a puncture needle according to a modification of the puncture needle illustrated in FIGS. 1A-1D, in which FIG. 7A is a plan view of a front side, FIG. 7B is a side view, FIG. 7C is a plan view of a back side, and FIG. 7D is a perspective view.

FIG. 8 is a flowchart illustrating a method for manufacturing a puncture needle according to an embodiment of the present invention.

FIGS. 9A-9C are general views illustrating an outline of the blade surface forming step illustrated in FIG. 8, in which FIG. 9A is a general view of a first blade surface portion forming step, FIG. 9B is a general view of a second blade surface portion forming step, and FIG. 9C is a general view of a third blade surface portion forming step.

FIGS. 10A-10D are diagrams illustrating a puncture needle according to a modification of the puncture needle illustrated in FIGS. 1A-1D, in which FIG. 10A is a plan view of a front side, FIG. 10B is a side view, FIG. 10C is a plan view of a back side, and FIG. 10D is a perspective view.

DETAILED DESCRIPTION

Figure 1A:
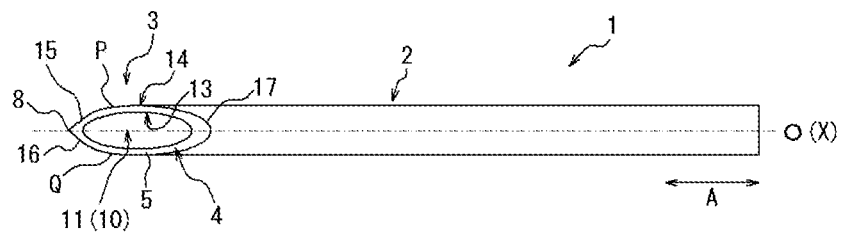

Hereinafter, a medical puncture needle and a method for manufacturing the puncture needle according to embodiments of the present invention will be described with reference to FIGS. 1 to 11. In the drawings, common members are denoted by the same reference numerals.

First Embodiment

Figure 1B:
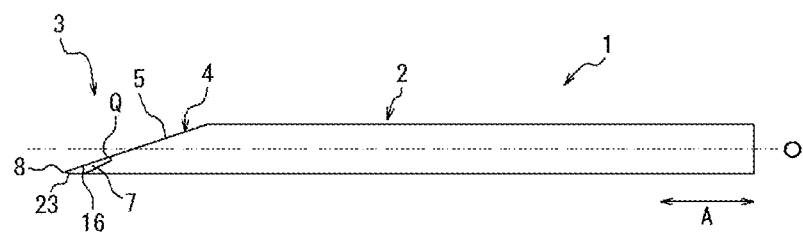
Figure 1C:
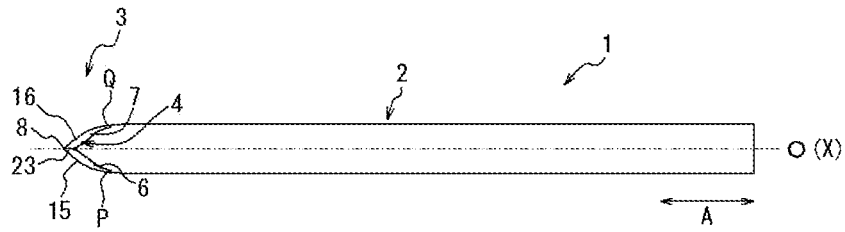
Figure 1D:
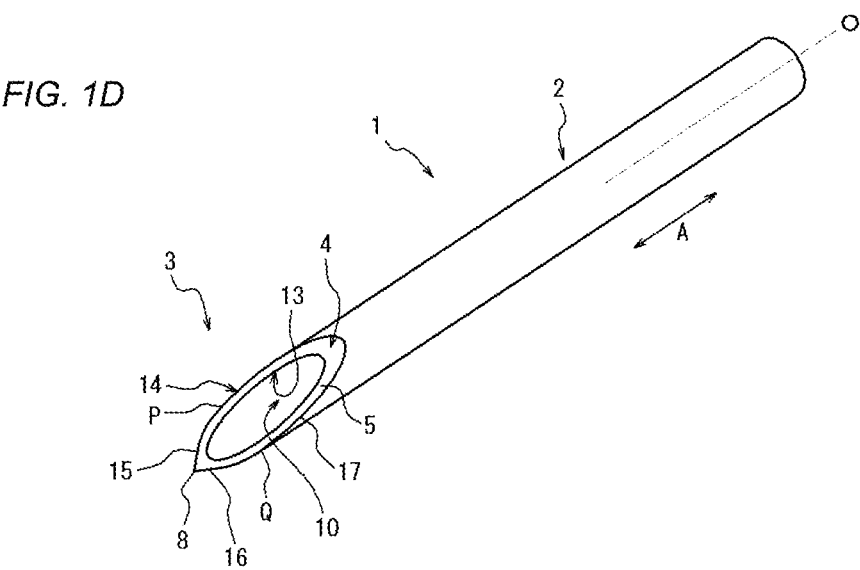

First, a puncture needle 1 as one embodiment of a medical puncture needle according to the present invention will be described. FIGS. 1A-1D are diagrams illustrating the puncture needle 1. Specifically, FIG. 1A is a plan view of a front side of the puncture needle 1, FIG. 1B is a side view of the puncture needle 1, and FIG. 1C is a plan view of a back side of the puncture needle 1. FIG. 1D is a perspective view of the puncture needle 1.

As illustrated in FIGS. 1A to 1D, the puncture needle 1 includes a main body portion 2 and a distal end portion 3, and sections a hollow portion 10 communicating from the main body portion 2 to the distal end portion 3.

The main body portion 2 is a hollow rod-like body, namely, a tubular pipe body continuous with the distal end portion 3. More specifically, the main body portion 2 is a pipe body continuous with the distal end portion 3 and having a substantially circular cross sectional outline. Here, the "cross section" of the "cross sectional outline" represents a transverse cross section orthogonal to a center axis O of the main body portion 2.

As illustrated in FIGS. 1A to 1D, the distal end portion 3 includes a blade surface 4, and the blade surface 4 includes a first blade surface portion 5 as a front side blade surface and includes a second blade surface portion 6 and a third blade surface portion 7 as back side blade surfaces. In other words, the puncture needle 1 according to the present embodiment includes the blade surface 4 formed with back-cut processing.

The first blade surface portion 5 is constituted with a plane inclined with respect to the center axis O of the main body portion 2 and extending to a needle point 8. The second blade surface portion 6 and the third blade surface portion 7 are formed of curved surfaces, and intersect each other to be a ridgeline and form a blade edge 23 having the needle point 8 as one end by the ridgeline on a back side of the first blade surface portion 5. Note that the "needlepoint" represents the distal end of the puncture needle 1 in an axial direction A of the center axis O of the main body portion 2 (hereinafter simply referred to as "center axis direction A").

The first blade surface portion 5 is a plane that is inclined at a predetermined angle such as 12 degrees or 18 degrees with respect to the center axis O, and an inner edge 13 of the first blade surface portion 5 sections an opening 11 being one end of the hollow portion 10 on the distal end portion 3 side. An outer edge 14 of the first blade surface portion 5 is formed with a blade edge 15 and a blade edge 16 having the needle point 8 as one end, and a main body portion side outer edge portion 17. Details of the outer edge 14 of the first blade surface portion 5 will be described below.

The second blade surface portion 6 and the third blade surface portion 7 have shapes symmetrical with respect to a virtual plane passing through the needle point 8 and including the center axis O, and the second blade surface portion 6 and the third blade surface portion 7 intersect each other to be a ridgeline and form a blade edge 23 having the needle point 8 as one end by the ridgeline, on the needle point 8 side in the center axis direction A. Note that the blade edge 23 is formed linearly and the blade edge 23 also extends on the virtual plane. In the present embodiment, the virtual plane is a plane perpendicular to the first blade surface portion 5. Hereinafter, for convenience of description, the virtual plane that is a virtual plane passing through the needle point 8 and including the center axis O will be simply referred to as a "center plane X".

The second blade surface portion 6 and the first blade surface portion 5 intersect each other to be a ridgeline and form the blade edge 15 having the needle point 8 as one end by the ridgeline. The blade edge 15 is a portion of the outer edge 14 of the first blade surface portion 5 and extends from the needle point 8 to a terminal point P on the outer edge 14.

Furthermore, the third blade surface portion 7 and the first blade surface portion 5 intersect each other to be a ridgeline and form the blade edge 16 having the needle point 8 as one end by the ridgeline. The blade edge 16 is also a portion of the outer edge 14 of the first blade surface portion 5 and extends from the needle point 8 to a terminal point Q on the outer edge 14.

Hereinafter, for convenience of description, the blade edge 23 formed by the ridgeline on which the second blade surface portion 6 and the third blade surface portion 7 intersect each other on the needle point 8 side will be referred to as "a first blade edge 23", the blade edge 15 formed by the ridgeline on which the first blade surface portion 5 and the second blade surface portion 6 intersect each other will be referred to as "a second blade edge 15", and the blade edge 16 formed by the ridgeline on which the first blade surface portion 5 and the third blade surface portion 7 intersect each other will be referred to as "a third blade edge 16".

With this configuration, at the time of puncturing from the surface of the living body with the puncture needle 1, the first blade edge 23, the second blade edge 15, and the third blade edge 16 act so as to incise the skin and reduce penetration resistance.

The second blade surface portion 6 changes the angle with respect to the center plane X on a cross section orthogonal to the center axis direction A depending on the position in the center axis direction A. Specifically, the second blade surface portion 6 is constituted with a curved surface similar to a helical surface, for example, extending in a twisted manner toward the needle point 8 side in the center axis direction A. Similarly, the third blade surface portion 7 is constituted with a curved surface similar to a helical surface, for example, extending in a twisted manner toward the needle point 8 side in the center axis direction A. As described above, the second blade surface portion 6 and the third blade surface portion 7 have symmetrical shapes with respect to the center plane X, and the twisting directions of the second blade surface portion 6 and the third blade surface portion 7 toward the needle point 8 side are opposite to each other.

More specifically, each of the second blade surface portion 6 and the third blade surface portion 7 is constituted with a curved surface in which an angle $\gamma$ with respect to the center plane X in a cross section orthogonal to the center axis direction A gradually increases toward the needle point 8 side in the center axis direction A. By forming the second blade surface portion 6 into this curved surface, it is possible to easily obtain a longer length of the second blade edge 15 as compared with a configuration in which the second blade surface portion is a plane. By forming the third blade surface portion 7 into this curved surface, it is possible to easily obtain a length of the third blade edge 16 that is longer as compared with a configuration in which the third blade surface portion is a plane.

Moreover, by forming the second blade surface portion 6 into the above-described curved surface, it is possible to suppress a case where the thickness of the needle at a position of formation of the second blade surface portion 6 becomes excessively thin as compared with the configuration in which the second blade surface portion is formed into a plane, making it possible to suppress degradation of the strength of the needle. Furthermore, capability of suppression of a case where the thickness becomes excessively thin thickness leads to suppression of defective products in the manufacturing process. Furthermore, as compared with the configuration in which the second blade surface portion is formed into a plane, it is possible to obtain a large area for the second blade surface portion 6, leading to enhanced rectilinearity. Similarly, these apply to the case where the third blade surface portion 7 is the above-described curved surface.

While the puncture needle 1 according to the present embodiment is configured such that both the second blade surface portion 6 and the third blade surface portion 7 are constituted with curved surfaces in which the angle $\gamma$ with respect to the center plane X in a cross section orthogonal to the center axis direction A gradually increases toward the needle point 8 side in the center axis direction A, it is also allowable to configure such that any one of the second blade surface portion 6 and the third blade surface portion 7 is constituted with such a curved surface while the other is constituted with a plane or a curved surface having another surface shape. With a configuration, however, used in the present embodiment, in which both the second blade surface portion 6 and the third blade surface portion 7 are constituted with curved surfaces in which the angle $\gamma$ with respect to the center plane X in a cross section orthogonal to the center axis direction A gradually increases toward the needle point 8 side in the center axis direction A, it is possible to obtain further longer length being the sum of the length of the second blade edge 15 and the length of the third blade edge 16, that is, being the length from the terminal point P through the needle point 8 to the terminal point Q on the outer edge 14 of the first blade surface portion 5. Details of the lengths of the second blade edge 15 and the third blade edge 16 will be described below (refer to FIGS. 3A-3E).

Herein, the "distal end portion" in the present application represents a portion in which a blade surface is formed in the center axis direction A of the puncture needle, while the "main body portion" represents a portion in which the blade surface is not formed on the puncture needle, in the center axis direction A. Accordingly, in the present embodiment, the distal end portion 3 corresponds to a portion in which the first blade surface portion 5, the second blade surface portion 6, and the third blade surface portion 7 are formed in the center axis direction A on the tubular member as an integral hollow rod-like member constituting the puncture needle 1. In the present embodiment, the main body portion 2 corresponds to a portion having a substantially circular cross sectional outline, in which the first blade surface portion 5, the second blade surface portion 6, and the third blade surface portion 7 are not formed in the center axis direction A on the integral tubular member constituting the puncture needle 1.

Examples of materials applicable as the puncture needle 1 in the present embodiment include a metal material such as stainless steel, aluminum or an aluminum alloy, titanium or a titanium alloy.

Hereinafter, individual configurations and characteristic portions according to the present embodiment will be described in detail.

[Main Body Portion 2]

The main body portion 2 according to the present embodiment is a pipe body having a uniform inner diameter of the inner circumferential surface and a uniform outer diameter of the outer circumferential surface in the center axis direction A, with an end portion on the opposite side of the distal end portion 3 side in the center axis direction A being connected to a medical instrument such as a syringe via a needle hub, or the like.

Note that while the present embodiment is a case where the inner circumferential surface (the inner circumferential surface of the main body portion 2 and the inner circumferential surface of the distal end portion 3) of the tubular member constituting the entire puncture needle 1 sections the hollow portion 10, with the inner diameter of the inner circumferential surface and the outer diameter of the outer circumferential surface of the tubular member being uniform in the center axis direction A, the configuration is not limited to this configuration. For example, alternatively, it is allowable to configure such that the inner diameter of the inner circumferential surface of the tubular member and the outer diameter of the outer circumferential surface of the tubular member gradually decrease toward the distal end portion 3 side in the center axis direction A. Still alternatively, for example, it is also possible to configure such that the outer diameter of the tubular member is tapered to gradually decrease toward the distal end portion 3 side in the center axis direction A and that the inner diameter of the tubular member is uniform in the center axis direction A. Furthermore, various configurations can be adopted for the inner and outer diameters of the tubular member constituting the puncture needle 1 in accordance with the usage of the puncture needle 1, including an exemplary case of providing a portion in which the inner diameter gradually decreases or gradually increases toward the distal end portion 3 side in the center axis direction A, in a portion of the region of the center axis direction A.

[First Blade Surface Portion 5 of Distal End Portion 3]

FIGS. 2A and 2B are enlarged views of the distal end portion 3 illustrated in FIGS. 1A and 1B, respectively. FIGS. 3A, 3B, 3C, 3D and 3E are cross sectional views taken along lines I-I, II-II, III-III, IV-IV and V-V in FIGS. 2A and 2B, respectively.

As illustrated in FIGS. 2A and 2B, the first blade surface portion 5 is a plane inclined with respect to the center axis direction A. One end of the first blade surface portion 5 is the needle point 8 while the other end is continuous with the outer circumferential surface of the main body portion 2 in the center axis direction A. The inclination angle of the first blade surface portion 5 with respect to the center axis direction A is greater than the inclination angle of the outer wall of the main body portion 2 with respect to the center axis direction A in the cross section orthogonal to the first blade surface portion 5. The present embodiment has a configuration in which the outer diameter of the tubular member constituting the puncture needle 1 is uniform in the center axis direction A, and the outer wall of the tubular member extends in the center axis direction A when viewed in a cross section orthogonal to the first blade surface portion 5. Accordingly, when the first blade surface portion 5 is inclined with respect to the center axis direction A, the inclination angle of the first blade surface portion 5 is greater than the inclination angle of the outer wall of the main body portion 2. In a case, however, where the tubular member constituting the puncture needle 1 is configured to have the outer diameter that gradually decreases or gradually increases toward the distal end portion 3 side in the center axis direction A, it is preferable that the first blade surface portion 5 is not merely inclined with respect to the center axis direction A, but also inclined with respect to the outer wall of the main body portion 2 in the cross section orthogonal to the first blade surface portion 5.

As illustrated in FIG. 2A, the outer edge 14 of the first blade surface portion 5 is constituted with the second blade edge 15, the third blade edge 16, and the protruding curved line-shaped main body portion side outer edge portion 17 connecting the terminal point P being one end of the second blade edge 15 on the main body portion 2 side with the terminal point Q being one end of the third blade edge 16 on the main body portion 2 side.

The second blade edge 15 and the third blade edge 16 are formed with curved lines. The second blade edge 15 and the main body portion side outer edge portion 17 are connected with each other by a continuous curved line without passing through an apex. In other words, the second blade edge 15 is continuous with the main body portion side outer edge portion 17 without forming an apex at a position of the terminal point P being also a connection point with the main body portion side outer edge portion 17.

Moreover, the third blade edge 16 and the main body portion side outer edge portion 17 are connected with each other with a continuous curved line without passing through an apex. In other words, the third blade edge 16 is continuous with the main body portion side outer edge portion 17 at the position of the terminal point Q being also a connection point with the main body portion side outer edge portion 17 without forming an apex.

In this manner, by suppressing formation of the apex at the positions of the terminal point P and the terminal point Q, it is possible to suppress the increase of the penetration resistance when the position of each of the terminal point P and the terminal point Q passes through the skin.

While it is preferable to configure so as not to form any apex at the positions of the terminal point P and the terminal point Q as in the present embodiment, it is also allowable to configure to form an apex of a level that would not increase the penetration resistance at the positions of the terminal point P and the terminal point Q.

[Second Blade Surface Portion 6 and Third Blade Surface Portion 7 of Distal End Portion]

As described above, each of the second blade surface portion 6 and the third blade surface portion 7 is constituted with a curved surface in which the angle γ with respect to the center plane X in a cross section orthogonal to the center axis direction A gradually increases toward the needle point 8 side in the center axis direction A. Hereinafter, details of the shapes of the second blade surface portion 6 and the third blade surface portion 7 will be described with reference to FIGS. 3A-3E.

FIG. 3A is a cross sectional view taken along line I-I in FIGS. 2A and 2B, that is, a cross section orthogonal to the center axis direction A at a position where the first blade surface portion 5 is formed in the center axis direction A and at the same time, at a position where the second blade surface portion 6 and the third blade surface portion 7 are not formed. As illustrated in FIG. 3A, an angle θ of the first blade surface portion 5 with respect to the center plane X in cross section I-I in FIGS. 2A and 2B is 90 degrees. In other words, in cross section I-I in FIGS. 2A and 2B, the first blade surface portion 5 extends linearly in a direction orthogonal to the center plane X. As described above, the first blade surface portion 5 is constituted with a plane inclined with respect to the center axis O, and thus, in FIGS. 3B to 3E to be referred to below, the angle θ of the first blade surface portion 5 with respect to the center plane X is constant at 90 degrees, similarly to FIG. 3A.

FIG. 3B illustrates a cross section taken along line II-II in FIGS. 2A and 2B, that is, a cross section passing through the terminal point P of the second blade edge 15 and the terminal point Q of the third blade edge 16 and orthogonal to the center axis direction A. In other words, FIG. 3B is a cross section orthogonal to the center axis direction A at the end portion of the second blade surface portion 6 and the third blade surface portion 7 on the main body portion 2 side. As illustrated in FIG. 3B, each of the second blade surface portion 6 and the third blade surface portion 7 in cross section II-II in FIGS. 2A and 2B is inclined at a predetermined acute angle γ1 with respect to the center plane X.

FIG. 3C is a cross sectional view taken along line III-III in FIGS. 2A and 2B, that is, a cross section orthogonal to the center axis direction A at a position on more toward the needle point 8 side in the center axis direction A than in the cross section illustrated in FIG. 3B and at the same time at a position where the opening 11 exists in the center axis direction A. In other words, FIG. 3C is a cross section orthogonal to the center axis direction A at a position where the first blade edge 23 is not formed in the center axis direction A and at the same time, at a position where the second blade edge 15 and the third blade edge 16 are formed. As illustrated in FIG. 3C, each of the second blade surface portion 6 and the third blade surface portion 7 in cross section III-III in FIGS. 2A and 2B is inclined at a predetermined angle γ2 with respect to the center plane X. The angle γ2 with respect to the center plane X in the cross section illustrated in FIG. 3C is an acute angle greater than the angle γ1 in the cross section illustrated in FIG. 3B.

FIG. 3D is a cross sectional view taken along line IV-IV in FIGS. 2A and 2B, that is, a cross section orthogonal to the center axis direction A at a position on more toward the needle point 8 side in the center axis direction A than in the cross section illustrated in FIG. 3C and at the same time at a position where the opening 11 exists in the center axis direction A. Similarly to FIG. 3C, FIG. 3D is a cross section orthogonal to the center axis direction A at a position where the first blade edge 23 is not formed in the center axis direction A and at the same time, at a position where the second blade edge 15 and the third blade edge 16 are formed. As illustrated in FIG. 3D, each of the second blade surface portion 6 and the third blade surface portion 7 in the cross section IV-IV in FIGS. 2A and 2B is inclined at a predetermined angle γ3 with respect to the center plane X. The angle γ3 is an acute angle greater than the angle γ1 in the cross section illustrated in FIG. 3B and greater than the angle γ2 in the cross section illustrated in FIG. 3C.

FIG. 3E illustrates a cross section taken along line V-V in FIGS. 2A and 2B, that is, a cross section orthogonal to the center axis direction A at a position where the first blade edge 23, the second blade edge 15, and the third blade edge 16 are formed in the center axis direction A. As illustrated in FIG. 3E, each of the second blade surface portion 6 and the third blade surface portion 7 in the cross section V-V in FIGS. 2A and 2B is inclined at a predetermined angle γ4 with respect to the center plane X. The angle γ4 is an acute angle greater than the angle γ1 in the cross section illustrated in FIG. 3B, greater than the angle γ2 in the cross section illustrated in FIG. 3C, and greater than the angle γ3 in the cross section illustrated in FIG. 3D.

Moreover, the second blade surface portion 6 and the third blade surface portion 7 are straight lines in a cross sectional view orthogonal to the center axis direction A, and the angle γ of each of the second blade surface portion 6 and the third blade surface portion 7 according to the present embodiment with respect to the center plane X in the cross section orthogonal to the center axis direction A gradually increases toward the needle point 8 side (in a closer position to the needle point 8) in the center axis direction A. Note that while FIGS. 3B to 3E illustrate the angles γ1 to γ4 of the third blade surface portion 7 with respect to the center plane X respectively, the angles of the second blade surface portion 6 with respect to the center plane X is also the same as the angles γ1 to γ4 of the third blade surface portion 7. The four cross sections in FIGS. 3B to 3E are merely examples to illustrate the size relationship between the above-described angles γ1, γ2, γ3, and γ4, and the size relationship of the above-described angles γ is not limited to these four cross sections.

Also note that as illustrated in FIGS. 3B to 3E, while the third blade surface portion 7 according to the present embodiment is a straight line in a cross sectional view orthogonal to the center axis direction A, the configuration is not limited to this particular configuration. Instead, for example, it is possible to configure such that the cross sectional view of the third blade surface portion, orthogonal to the center axis direction A, is formed with an arcuate curved line, and that the cross sectional view is formed with a straight line and an arcuate curved line continuous with this straight line. This also applies to the second blade surface portion in a similar manner. In this case, the angle γ of the second blade surface portion and the third blade surface portion indicates the angle formed by a straight line passing through an inner edge and an outer edge of each of the second blade surface portion and the third blade surface portion in the cross section orthogonal to the center axis direction A, and by one established virtual plane (center plane X in the present embodiment).

[First Blade Edge 23 of Distal End Portion 3]

As described above, the first blade edge 23 is formed by a ridgeline on which the second blade surface portion 6 and the third blade surface portion 7 intersect each other. As described above, the first blade edge 23 according to the present embodiment extends in the center plane X, and thus, the needle point 8 as one end of the first blade edge 23 is also located in the center plane X. That is, the puncture needle 1 according to the present embodiment is a hollow needle having a symmetrical configuration with respect to the center plane X.

As described above, the first blade edge 23 acts as a cutting edge that incises the skin when puncturing the human body with the puncture needle 1, making it possible to reduce the penetration resistance in the vicinity of the needle point 8 at the time of puncture.

[Second Blade Edge 15 and Third Blade Edge 16 of the Distal End Portion 3]

Next, details of the second blade edge 15 and the third blade edge 16 will be described. As described above, by constituting the second blade surface portion 6 with a curved surface in which the angle γ with respect to the center plane X in a cross section orthogonal to the center axis direction A gradually increases toward the needle point 8 side in the center axis direction A, it is possible to obtain the longer length of the blade edge of the second blade edge 15 compared with a case where the second blade surface portion is constituted with a plane. In other words, by constituting the second blade surface portion 6 with such a curved surface, it is possible to increase a circumferential extension range of the second blade edge 15 that can be expressed by a center angle β1 from the needle point 8 to the terminal point P around the center axis O when the puncture needle 1 is viewed from the needle point 8 side (refer to FIG. 3B). The circumferential extension range of the second blade edge 15 can be, for example, 50 degrees or more or 70 degrees or more, in the center angle β1.

By configuring the second blade surface portion 6 with the curved surface as described above, it is possible to obtain a longer length of the second blade edge 15, and thus, to increase a cutting width W1 (refer to FIG. 3B) capable of incising the skin with the second blade edge 15 at the time of puncturing with the puncture needle 1. In other words, the second blade surface portion 6 configured with the curved surface described above can increase the cutting width W1 of the second blade edge 15, as compared with the second blade surface portion configured with a plane. Therefore, after the second blade edge 15 has passed through the skin, it is possible to suppress the pushed-apart amount in the incision on the skin that is forcibly pushed apart by the outer surface of the main body portion 2 of the puncture needle 1 and by an outer surface of an outer needle attached to the circumference of the puncture needle 1 and having the puncture needle 1 as an inner needle and used for puncturing with the puncture needle 1. This makes it possible to reduce the pain sensed by the patient at the time of puncture. In addition, in a case where the cutting width W1 can be increased, it is possible to facilitate inserting a catheter covering the puncture needle 1 into the skin and a blood vessel in a case where the puncture needle 1 is used as an indwelling needle, for example, and to suppress rollover of the catheter at the time of puncture.

The above description on the second blade surface portion 6 can also be applied similarly to the case of the third blade surface portion 7. Specifically, by constituting the third blade surface portion 7 with a curved surface in which the angle γ with respect to the center plane X in a cross section orthogonal to the center axis direction A gradually increases toward the needle point 8 side in the center axis direction A, it is possible to obtain the longer length of the blade edge of the third blade edge 16 compared with a case where the third blade surface portion is constituted with a plane. In other words, by constituting the third blade surface portion 7 with such a curved surface, it is possible to increase a circumferential extension range of the third blade edge 16 that can be expressed by a center angle β2 from the needle point 8 to the terminal point Q around the center axis O when the puncture needle 1 is viewed from the needle point 8 side (refer to FIG. 3B). The circumferential extension range of the third blade edge 16 can be, for example, 50 degrees or more or 70 degrees or more, in the center angle β2.

By configuring the third blade surface portion 7 with the curved surface in this manner, it is possible to obtain a further longer length of the third blade edge 16, and thus, to increase a cutting width W2 (refer to FIG. 3B) capable of incising the skin with the third blade edge 16 at the time of puncturing with the puncture needle 1. In other words, the third blade surface portion 7 configured with the curved surface described above can increase the cutting width W2 of the third blade edge 16, as compared with the third blade surface portion configured with a plane as described above. Therefore, after the third blade edge 16 has passed through the skin, it is possible to suppress the amount of pushing apart in the incision on the skin that is forcibly pushed apart by the outer surface of the main body portion 2 of the puncture needle 1 and by an outer surface of an outer needle attached to the circumference of the puncture needle 1 having the puncture needle 1 as an inner needle and used for puncturing with the puncture needle 1. This makes it possible to reduce the pain sensed by the patient at the time of puncture. In addition, in a case where the cutting width W2 can be increased, it is possible to facilitate inserting a catheter covering the puncture needle 1 into the skin and a blood vessel in a case where the puncture needle 1 is used as an indwelling needle, for example, and to suppress rollover of the catheter at the time of puncture.

It is preferable to constitute the second blade surface portion 6 and the third blade surface portion 7 with the curved surfaces as in the present embodiment, because this would allow the sum of the cutting width W1 of the second blade edge 15 and the cutting width W2 of the third blade edge 16 to be further greater than in the case where solely any one of the two surfaces is constituted with the curved surface.

Figure 7A:
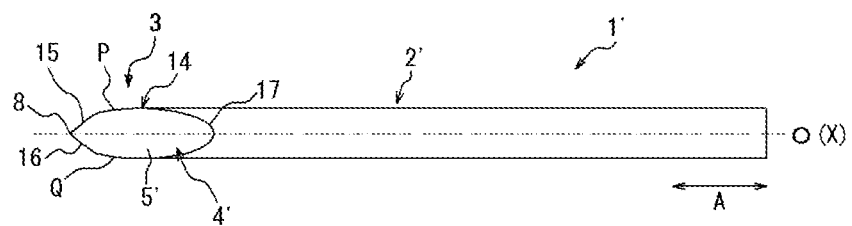
Figure 7B:
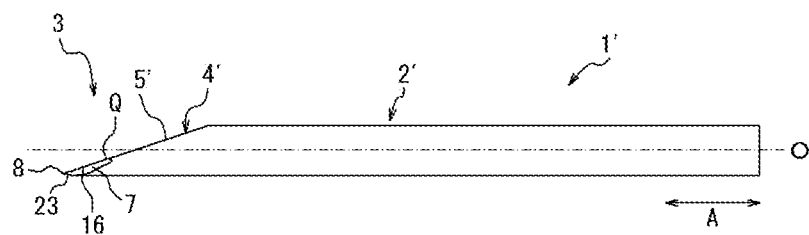
Figure 7C:
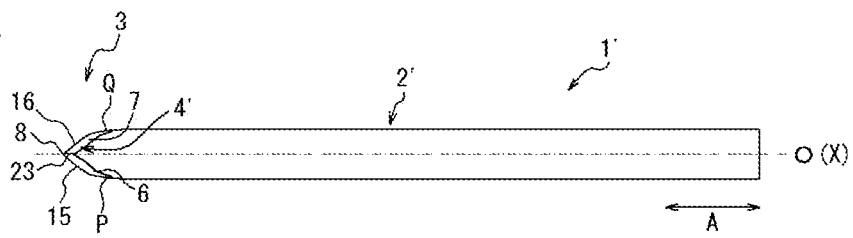
Figure 7D:
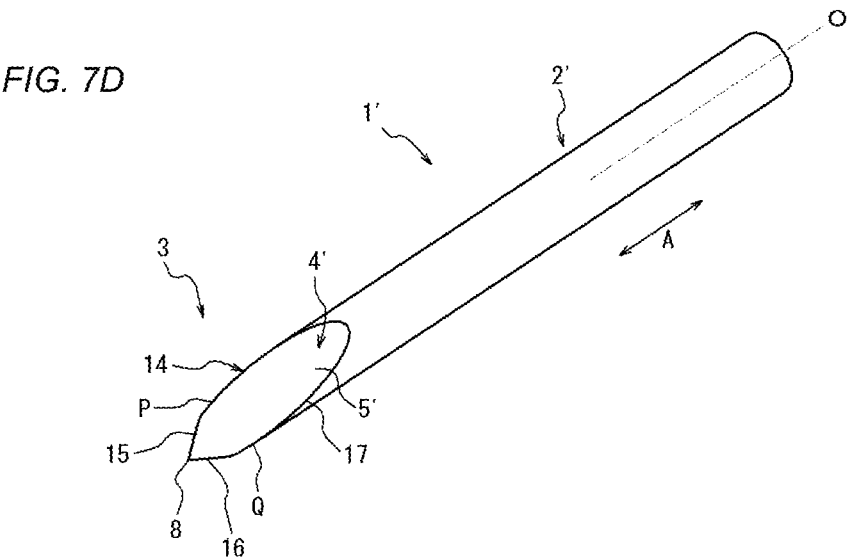

Note that while the puncture needle 1 of the present embodiment is a hollow needle that sections the hollow portion 10 inside, it is not limited to this configuration, and the needle may be a solid needle without a hollow portion. FIGS. 7A-7D are diagrams illustrating a puncture needle 1' according to a modification of the puncture needle 1 in the present embodiment, in which FIG. 7A is a plan view of a front side, FIG. 7B is a side view, FIG. 7C is a plan view of a back side, and FIG. 7D is a perspective view. As illustrated in FIGS. 7A-7D, the puncture needle 1' is a solid needle not sectioning a hollow portion therein, and the other configuration is similar to that of the puncture needle 1 of the present embodiment. Accordingly, in FIGS. 7A-7D, common portions to those of the puncture needle 1 are denoted by common reference numerals, and a detailed description thereof will be omitted. Since the puncture needle 1' illustrated in FIGS. 7A-7D does not section the hollow portion inside, a first blade surface portion 5' of a blade surface 4' is constituted with a plane inclined at a predetermined angle with respect to the center axis line O of a main body portion 2', and being a uniform plane with no opening formed at the center. Note that the main body portion 2' of the puncture needle 1 illustrated in FIGS. 7A-7D has a solid rod-like shape.

While the main body portion 2 of the puncture needle 1 according to the present embodiment has a sectional outline having a substantially circular shape in an arbitrary transverse section, the configuration is not limited to this configuration as long as the main body portion has a hollow rod-like or a solid rod-like shape. For example, the main body portion may have a cross sectional outline having a substantially elliptical shape in an arbitrary transverse section, and the main body portion may have a cross sectional outline having any of a substantially circular shape and a substantially elliptical shape in an arbitrary transverse section. Furthermore, the main body portion may have a portion partially including the cross sectional outline formed into a substantially circular shape or a substantially elliptical shape. Still further, the shape other than the circular shape may be any shape as long as it has a flat cross sectional outline in which the major axis and the minor axis are defined, and is not limited to the elliptical shape described above and it is possible to apply, for example, a rounded rectangle obtained by combining a semicircle to either of short sides of a rectangular.

FIGS. 10A-10D are diagrams illustrating a puncture needle 151 including a main body portion 152 having an arbitrary transverse cross sectional outline of a substantially circular shape or a substantially elliptical shape, in which FIG. 10A is a plan view of the front side of the puncture needle 151, FIG. 10B is a side view of the puncture needle 151, FIG. 10C is a plan view of the back side of the puncture needle 151, and FIG. 10D is a perspective view of the puncture needle 151.

The puncture needle 151 illustrated in FIGS. 10A-10D includes the main body portion 152 and the distal end portion 153, and sections a hollow portion 160 communicating from the main body portion 152 to the distal end portion 153.

The main body portion 152 is a hollow rod-like body, namely, a tubular pipe body continuous with the distal end portion 153. More specifically, the main body portion 152 includes a main body distal end portion 152a, a main body barrel portion 152b, and a linkage 152c. The main body distal end portion 152a has a substantially elliptical cross sectional outline continuous with the distal end portion 153. The main body barrel portion 152b is located on the proximal end side of the main body distal end portion 152a and has a substantially circular cross sectional outline. The linkage 152c is located between the main body distal end portion 152a and the main body barrel portion 152b and connects the main body distal end portion 152a and the main body barrel portion 152b.

The main body distal end portion 152a has a substantially elliptical cross sectional outline with a major axis having a width S1 in the plan view of FIGS. 10A and 10C and a minor axis having a width S2 in a side view in FIG. 10B. As illustrated in FIGS. 10A and 10C, the width S1 as the major axis of the main body distal end portion 152a is greater than the outer diameter of the main body barrel portion 152b, and the width S2 as the minor axis of the main body distal end portion 152a is smaller than the outer diameter of the main body barrel portion 152b. Moreover, the center axis of the main body distal end portion 152a substantially matches the center axis of the main body barrel portion 152b, and the center axis O of the main body portion 152 is substantially a straight line. Accordingly, the linkage 152c has a tapered shape gradually increasing toward the distal end portion 153 side in the center axis direction A, in plan views of the front side and the back side (refer to FIGS. 10A and 10C) while gradually decreasing toward the distal end portion 153 side in the center axis direction A in a side view (refer to FIG. 10B). Note that the center plane X including the center axis O and a needle point 158 is a plane including the minor axis in a cross section orthogonal to the center axis direction A of the main body distal end portion 152a.

As illustrated in FIGS. 10A to 10D, the distal end portion 153 is continuous with the main body distal end portion 152a having cross sectional outline of substantially elliptical. The distal end portion 153 includes a blade surface 154. The blade surface 154 includes a first blade surface portion 155 as a front side blade surface and includes a second blade surface portion 156 and a third blade surface portion 157 as back side blade surfaces.

The first blade surface portion 155 is constituted with a plane inclined with respect to the center axis O of the main body portion 152 and extending to the needle point 158. The second blade surface portion 156 and the third blade surface portion 157 are formed of curved surfaces, and intersect each other to be a ridgeline and form a blade edge 173 having the needle point 158 as one end by the ridgeline on a back side of the first blade surface portion 155. The second blade surface portion 156 and the third blade surface portion 157 are located at positions across the center plane X including the minor axis.

Similarly to the shape of the first blade surface portion 5 of the above-described puncture needle 1, the shape of the first blade surface portion 155 illustrated in FIGS. 10A-10D is a plane inclined at a predetermined angle such as 12 degrees and 18 degrees with respect to the center axis O, and thus, description is omitted herein.

Moreover, similarly to the shapes of the second blade surface portion 6 and the third blade surface portion 7 of the above-described puncture needle 1, each of the shapes of the second blade surface portion 156 and the third blade surface portion 157 illustrated in FIGS. 10A-10D is formed with a curved surface in which the angle γ with respect to the center plane X in a cross section orthogonal to the center axis direction A gradually increases toward the needle point 158 side in the center axis direction A, and description thereof is omitted herein.

The puncture needle 151 illustrated in FIGS. 10A-10D differs from the above-described puncture needle 1 in the outline of the cross section orthogonal to the center axis direction A of the main body portion 152 and the distal end portion 153. Specifically, the maximum thickness of the distal end portion 153 in a side view of the puncture needle 151 (refer to FIG. 10B) is thinner than the maximum thickness of the distal end portion 3 of the above-described puncture needle 1 in a side view (refer to FIG. 1B). In the puncture needle 151 illustrated in FIGS. 10A-10D, a minor axis of the main body distal end portion 152a in a cross section orthogonal to the center axis direction A is included in the center plane X. This configuration makes it easier to achieve the puncture needle 151 having a shorter blade surface length M, as compared with the above-described puncture needle 1.

Figure 11A:
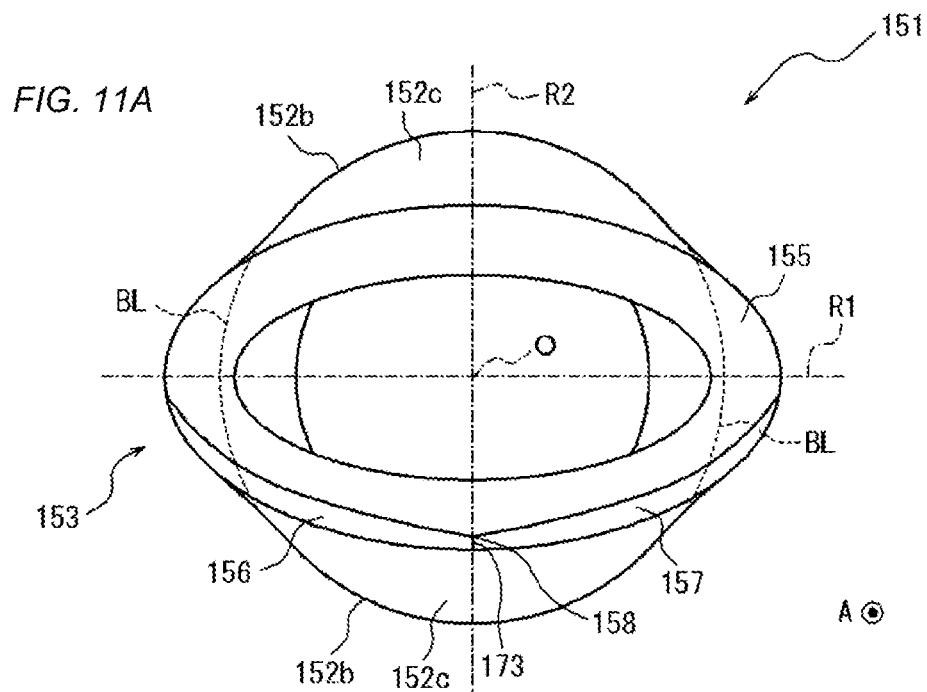
FIG. 11A is a view of the puncture needle illustrated in FIG. 10 seen from the needle point side.

FIG. 11A is a diagram of the puncture needle 151 illustrated in FIGS. 10A-10D as viewed from the needle point 158 side. In FIG. 11A, "R1" indicated by a one-dot chain line indicates the major axis and "R2" indicates the minor axis. As illustrated in FIG. 11A, when viewed in the center axis direction A, the needle point 158 is located inside the outer circumference of the main body barrel portion 152b (for convenience of description, a portion of the outer circumference invisible at a viewpoint of FIG. 11A is represented by broken line BL).

That is, the puncture needle 151 includes the distal end portion 153 having a flat cross sectional outline including the needle point, the main body distal end portion 152a having a flat cross sectional outline continuous with the distal end portion 153 and defined by the major axis R1 and the minor axis R2, and the main body barrel portion 152b located on more toward the proximal end side from the main body distal end portion 152a and having a substantially circular cross sectional outline. The distal end portion 153 includes the blade surface 154. The blade surface 154 includes the first blade surface portion 155, the second blade surface portion 156, and the third blade surface portion 157. The first blade surface portion 155 is inclined with respect to the center axis O of the main body barrel portion 152b and extends to the needle point 158. The second blade surface portion 156 and the third blade surface portion 157 are formed on the back side of the first blade surface portion 155. The needle point 158 is located inside the outer circumference of the main body barrel portion 152b when viewed in the center axis direction A.

By arranging the position of the needle point 158 as viewed in the center axis direction A at this position, it is possible to form the inclination angle of the first blade surface portion 155 with respect to the center axis direction A to be smaller than the inclination angle of the first blade surface portion with respect to the center axis direction A in the above-described comparative configuration in which the position of the needle point viewed in the center axis direction A is located on the outer circumference or outside the outer circumference of the main body barrel portion 152b, while the length of each of the first blade surface portion 155 in the center axis direction A can be formed to be equal to the length of the first blade surface portion in the center axis direction A in the above-described comparative configuration. This configuration makes it easier to achieve the first blade surface portion 155 capable of reducing the pressing force applied from the body tissue toward the back side during the puncture. That is, this configuration makes it easier to achieve the puncture needle 151 capable of enhancing rectilinearity.

Moreover, as described above, by arranging the position of the needle point 158 when viewed in the center axis direction A to be the position inside the outer circumference of the main body barrel portion 152b, it is possible to further decrease a blade tip angle α while the first blade surface portion 155 in the center axis direction A is formed to have a same length as compared with the configuration in which the position of the needle point when viewed in the center axis direction A is on the outer circumference of the main body barrel portion 152b or outside the outer circumference of the main body barrel portion 152b. This configuration makes it easier to achieve the puncture needle 151 having a thin blade tip and capable of alleviating the penetration resistance at the blade tip. Note that the blade tip angle α represents an angle at which the blade edge 173 crosses a surface on the front side opposite side of the blade surface 173 at the needle point 158 in a side view (refer to FIG. 10B) of the puncture needle 151.

Figure 11B:
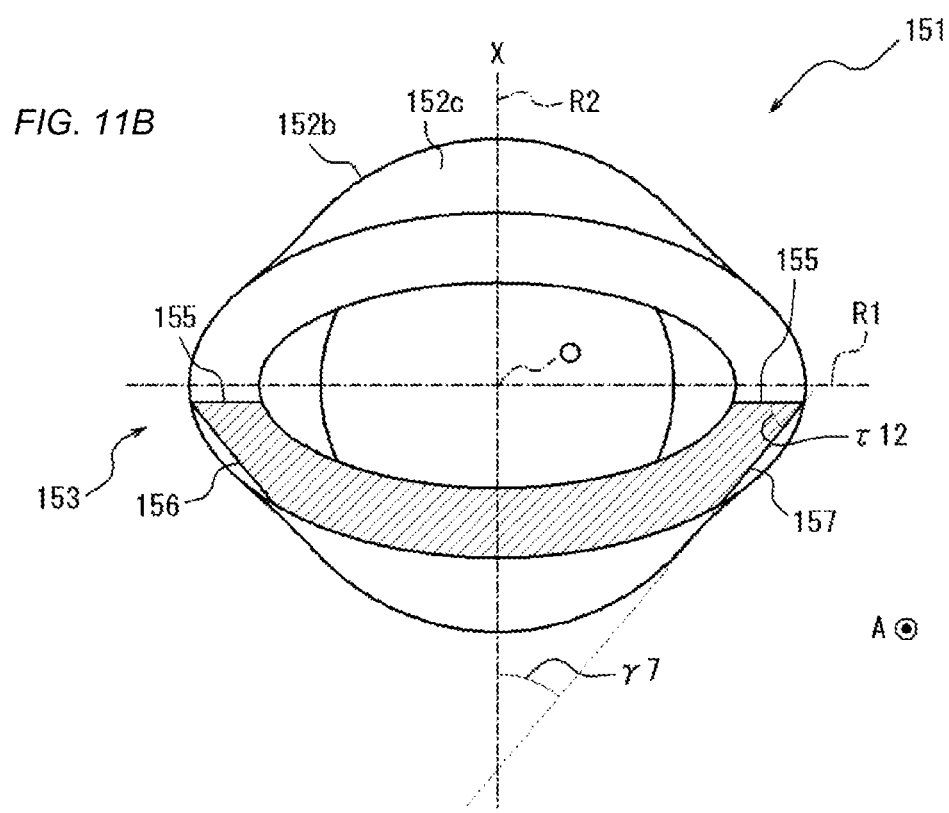
FIG. 11B is a cross section taken along line XII-XII in FIG. 10A.

Furthermore, while the needle point 158 is formed in the vicinity of one end position in a minor axis direction (direction parallel to the minor axis R2 in FIG. 11A) when viewed in the center axis direction A (refer to FIG. 11A), the position is not limited to the position of the needle point 158 illustrated in FIG. 11A as long as it is located inside the outer circumference of the main body barrel portion 152b when viewed in the center axis direction A (refer to FIG. 11A). Still, it is preferable that the needle point 158 is formed at a position of one end in the minor axis direction, or in the vicinity of the position of one end in the minor axis direction (hereinafter, the position of one end in the minor axis direction and the position in the vicinity thereof will be referred to as "position on one end side in the minor axis direction") as illustrated in FIGS. 10 and 11). With this arrangement, it is possible to form the second blade surface portion 156 and the third blade surface portion 157 at a position with a large radius of curvature in the distal end portion 153 having a flat cross sectional outline as the elliptical shape illustrated in FIG. 11A, when viewed in the center axis direction A. This makes it possible to obtain the long length of the blade edge constituted with the outer edge of each of the second blade surface portion 156 and the third blade surface portion 157, and makes it easier to obtain the length of the cutting edge having an intersecting angle τ (refer to "τ12" in FIG. 11B) of a predetermined angle (e.g., 60 degrees) or less.

More specifically, by forming each of the second blade surface portion 156 and the third blade surface portion 157 at a position having a large radius of curvature, it is possible to achieve a configuration in which the acute angle γ of the second blade surface portion 156 and the third blade surface portion 157 with respect to the center plane X including the needle point 158 (refer to "γ7" in FIG. 11B) is changed in accordance with the position in the center axis direction A within a broader angular range as compared with a configuration in which the needle point 158 is formed at a position of one end side in a major axis direction (direction parallel to the major axis R1 in FIG. 11A). In other words, it is possible to form each of the second blade surface portion 156 and the third blade surface portion 157 into a curved surface further extending closely along the major axis R1 as compared with the configuration in which the needle point 158 is formed at the position on one end side in the major axis direction (direction parallel to the major axis R1 in FIG. 11A). This makes it possible to obtain the longer length of the cutting edge portion having the intersecting angle τ (refer to "τ12" in FIG. 11B) of a predetermined angle (e.g., 60 degrees) or less among the blade edge constituted with the outer edge of each of the second blade surface portion 156 and the third blade surface portion 157.

The blade edge constituted with the outer edge of each of the second blade surface portion 156 and the third blade surface portion 157 is a portion formed by a ridgeline on which each of the second blade surface portion 156 and the third blade surface portion 157 intersects the first blade surface portion 155. The term "cutting edge" as used herein refers to a portion ranging from the needle point 158 to a predetermined length having the intersecting angle τ (refer to "τ12" in FIG. 11B) being a predetermined angle (for example, 60 degrees) or less among the blade edge constituted with the outer edge of each of the second blade surface portion 156 and the third blade surface portion 157. The intersecting angle τ represents an angle formed between the second blade surface portion 156 and the first blade surface portion 155, and between the third blade surface portion 157 and the first blade surface portion 155, in a cross section orthogonal to the center axis direction A. This cutting edge, together with the blade edge 173, incises the skin at the time of puncture. Therefore, by obtaining the long length of the cutting edge at the blade edge constituted with the outer edge of each of the second blade surface portion 156 and the third blade surface portion 157, it is possible to reduce the pain sensed by the patient caused by the outer edge of each of the second blade surface portion 156 and the third blade surface portion 157 passing on the patient at the time of puncture.

It is preferable that the blade edge constituted with the outer edge of at least one blade surface portion of the second blade surface portion 156 and the third blade surface portion 157 extends to the outside of the outer circumference of the main body barrel portion 152b when the distal end portion 153 is viewed in the center axis direction A (refer to FIG. 11A). In the example illustrated in FIG. 11A, the both blade edges constituted with the outer edges of both the second blade surface portion 156 and the third blade surface portion 157 extend to the outside of the outer circumference of the main body barrel portion 152b. As described above, the distal end portion 153 of the puncture needle 151 has a flat cross sectional outline, and the needle point 158 is formed at a position on one end side in the minor axis direction (direction parallel to the minor axis R2 in FIG. 11A). Therefore, as described above, it is easy to provide a long length of the cutting edge at which the intersecting angle τ is a predetermined angle (for example, 60 degrees) or less on the blade edge constituted with the outer edge of each of the second blade surface portion 156 and the third blade surface portion 157. In addition, as illustrated in FIG. 11A, by adopting the configuration in which the blade edge constituted with the outer edge of each of the second blade surface portion 156 and the third blade surface portion 157 extends to the outside of the outer circumference of the main body barrel portion 152b when the distal end portion 153 is viewed in the center axis direction A, it is possible to easily achieve a cutting edge long in the major axis direction (direction parallel to the major axis R1 in FIG. 11A) extending from the needle point 158 to the outside of the outer circumference of the main body barrel portion 152b when the distal end portion 153 is viewed in the center axis direction A. Achievement of such a long cutting edge can alleviate the pain sensed by the patient caused by the outer edge of each of the second blade surface portion 156 and the third blade surface portion 157 passing on the patient at the time of puncture.

FIG. 11B is a cross sectional view taken along line XII-XII in FIG. 10A. In the cross section illustrated in FIG. 11B, the blade edge constituted with the outer edge of each of the second blade surface portion 156 and the third blade surface portion 157 forms a cutting edge having the intersecting angle τ12 of a predetermined angle (for example, 60 degrees) or less. That is, the blade edge constituted with the outer edge of each of the second blade surface portion 156 and the third blade surface portion 157 forms a cutting edge long in the major axis direction (direction parallel to the major axis R1 in FIG. 11A) extending from the needle point 158 to the outside of the outer circumference of the main body barrel portion 152b when the distal end portion 153 is viewed in the center axis direction A.

Furthermore, as in the example illustrated in FIG. 11A, it is preferable that the outer edge of at least one of the second blade surface portion 156 and the third blade surface portion 157 extends from the needle point 158 to reach the position at which the width of the distal end portion 153 is maximized in the major axis direction when the distal end portion 153 is viewed in the center axis direction A. In addition, as in the example illustrated in FIG. 11A, it is preferable that the outer edges of both the second blade surface portion 156 and the third blade surface portion 157 extend from the needle point 158 to reach the position at which the width of the distal end portion 153 is maximized in the major axis direction when the distal end portion 153 is viewed in the center axis direction A. With such a configuration, the cutting edge can be formed over the entire width of the distal end portion 153 in the major axis direction. By forming a cutting edge having the intersecting angle τ of a predetermined angle (for example, 60 degrees) or less over the entire width of the distal end portion 153 in the major axis direction, it is possible to alleviate the pain sensed by the patient caused by the distal end portion 153 passing on the patient at the time of puncture.

Next, a puncture needle 101 different from the above-described embodiment will be described.

FIGS. 4A-4D are diagrams illustrating the puncture needle 101. Specifically, FIG. 4A is a plan view of a front side of the puncture needle 101, FIG. 4B is a side view of the puncture needle 101, FIG. 4C is a plan view of a back side of the puncture needle 101. FIG. 4D is a perspective view of the puncture needle 101. FIGS. 5A and 5B are enlarged views of a distal end portion 103 illustrated in FIGS. 4A and 4B, respectively. FIGS. 6A, 6B, 6C, 6D, 6E, and 6F are cross sectional views taken along lines VI-VI, VII-VII, VIII-VIII, IX-IX, X-X, and XI-XI in FIGS. 5A and 5B, respectively.

As illustrated in FIGS. 4A to 4D, the puncture needle 101 includes a main body portion 102 and the distal end portion 103, and sections a hollow portion 110 communicating from the main body portion 102 to the distal end portion 103. The distal end portion 103 includes a blade surface 104. The blade surface 104 includes a first blade surface portion 105 as a front side blade surface and includes a second blade surface portion 106 and a third blade surface portion 107 as back side blade surfaces, formed on the back side of the front side blade surface. In other words, the puncture needle 101 includes the blade surface 104 formed with back-cut pro- cessing. The configuration of the main body portion 102 is similar to that of the main body portion 2 of the above-described puncture needle 1.

The first blade surface portion 105 includes a first bevel surface 105a, a second bevel surface 105b, and a third bevel surface 105c, being formed by curved surfaces.

The first bevel surface 105a and the second bevel surface 105b intersect each other to be a ridgeline and form a blade edge 109 having a needle point 108 as one end by the ridgeline. Each of the first blade bevel surface 105a and the second bevel surface 105b is continuous with the third bevel surface 105c on the main body portion 102 side in the center axis direction A. In addition, the first bevel surface 105a and the second bevel surface 105b section an opening 111, which is one end on the distal end portion 103 side of the hollow portion 110.

The third bevel surface 105c is continuous with the outer circumferential surface of the main body portion 102 on the main body portion 102 side in the center axis direction A and continuous with the first bevel surface 105a and the second bevel surface 105b on the needle point 108 side in the center axis direction A.

As can be seen from the side views in FIGS. 4B and 5B, the angle of the second bevel surface 105b in the cross section orthogonal to the center axis direction A changes depending on the position in the center axis direction A. Specifically, in FIGS. 4B and 5B, while merely an outer edge of the second bevel surface 105b can be visually recognized at a position where the second bevel surface 105b and the third bevel surface 105c are continuous with each other in the center axis direction A, the second bevel surface 105b can be visually recognized at a position where the blade edge 109 is formed in the center axis direction A. That is, the second bevel surface 105b is constituted with a curved surface similar to a helical surface, for example, extending in a twisted manner from the position continuous with the third bevel surface 105c toward the needle point 108 in the center axis direction A. Similarly to the second bevel surface 105b, the first bevel surface 105a is also constituted with a curved surface extending in a twisted manner from the position continuous with the third bevel surface 105c toward the needle point 108 in the center axis direction A. Note that the directions of twisting of the first bevel surface 105a and the second bevel surface 105b toward the needle point 108 side are opposite to each other.

In other words, in a case where one virtual plane including the center axis O of the main body portion 102 is established, each of the first bevel surface 105a and the second bevel surface 105b is constituted with a curved surface in which the angle θ with respect to the one virtual plane in a cross section orthogonal to the center axis direction A gradually decreases toward the needle point 108 side in the center axis direction A. In short, the puncture needle 101 is a puncture needle capable of defining such one virtual plane.

Here, the puncture needle 101 includes one plane that can be defined as the above-described "virtual plane". Specifically, the puncture needle 101 according to the present embodiment enables the above-described "virtual plane" to be established in the center plane X including the center axis O and the needle point 108, and is configured such that each of the first bevel surface 105a and the second bevel surface 105b is constituted with a curved surface in which the angle θ1 with respect to the center plane X in a cross section orthogonal to the center axis direction A gradually decreases toward the needlepoint 108 side in the center axis direction A. Note that the center plane X is a plane including not solely the needle point 108 but also the blade edge 109 and a blade edge 123 to be described below.

While the puncture needle 101 is configured such that both the first bevel surface 105*a* and the second bevel surface 105*b* are constituted with curved surfaces in which the angle θ1 with respect to the center plane X in a cross section orthogonal to the center axis direction A gradually decreases toward the needlepoint 108 side in the center axis direction A, it is also allowable to configure such that any one of the first bevel surface 105*a* and the second bevel surface 105*b* is constituted with such a curved surface while the other is constituted with a plane or a curved surface having another surface shape. Still, with a configuration in which both the first bevel surface 105*a* and the second bevel surface 105*b* are constituted with curved surfaces in which the angle θ with respect to the center plane X in a cross section orthogonal to the center axis direction A gradually decreases toward the needle point 108 side in the center axis direction A, it is possible to facilitate achieving the first blade surface portion 105 that is unlikely to form a ridgeline (junction) having a possibility of becoming puncturing resistance, between the first bevel surface 105*a*/second bevel surface 105*b* and the third bevel surface 105*c*.

Details of the curved surface shapes of the first bevel surface 105*a* and the second bevel surface 105*b* will be described below (refer to FIGS. 6A-6F or the like).

The third bevel surface 105*c* is constituted with a protruding curved surface continuous with each of the first bevel surface 105*a* and the second bevel surface 105*b*. Specifically, the third bevel surface 105*c* is a protruding curved surface inclined so as to come closer to the center axis O toward the needle point 108 in the center axis direction A as in the side view in FIG. 5B, and the angle θ with respect to the center plane X in the cross section orthogonal to the center axis direction A is substantially constant regardless of the position in the center axis direction A.

More specifically, as illustrated in FIGS. 4 and 5, the third bevel surface 105*c* includes a distal end side portion 140*a* continuous with the first bevel surface 105*a* and the second bevel surface 105*b* on the needle point 108 side in the center axis direction A, and includes a proximal end side portion 140*b* continuous with the main body portion 102 side of the distal end side portion 140*a* in the center axis direction A. The distal end side portion 140*a* and the proximal end side portion 140*b* are formed with protruding curved surfaces having different curvatures in a side view (refer to FIGS. 4B and 5B). Moreover, each of the distal end side portion 140*a* and the proximal end side portion 140*b* is constituted with a curved surface having the substantially constant angle θ with respect to the center plane X in a cross section orthogonal to the center axis direction A, regardless of the position in the center axis direction A. The portion between the first bevel surface 105*a*/second bevel surface 105*b* and the distal end side portion 140*a*, and the portion between the distal end side portion 140*a* and the proximal end side portion 140*b* are smoothly continuous portions so as not to form a ridgeline.

In other words, the distal end side portion 140*a* and the proximal end side portion 140*b* having different curvatures of the puncture needle 101 in a side view (refer to FIGS. 4B and 5B) are continuously arranged in the center axis direction A, so as not to from a ridgeline to be penetration resistance between the first bevel surface 105*a*/second bevel surface 105*b* and the third bevel surface 105*c*. That is, the distal end side portion 140*a* of the third bevel surface 105*c* is a connecting curved surface for smoothly connecting the first bevel surface 105*a* and the second bevel surface 105*b* to the proximal end side portion 140*b* of the third bevel surface 105*c*, with the curvature in a side view being greater than the curvature of the proximal end side portion 140*b*.

More specifically, as illustrated in FIG. 5A, the distal end side portion 140*a* is constituted with a first connecting curved surface 130*a* and a second connecting curved surface 130*b*. The first connecting curved surface 130*a* is located between the first bevel surface 105*a* and the proximal end side portion 140*b* in the center axis direction A. The second connecting curved surface 130*b* is located between the second bevel surface 105*b* and the proximal end side portion 140*b* in the center axis direction A. Note that while FIG. 5A includes a line representing a boundary line at each of the portion between the first bevel surface 105*a* and the first connecting curved surface 130*a* of the distal end side portion 140*a*, the portion between the second bevel surface 105*b* and the second connecting curved surface 130*b* of the distal end side portion 140*a*, the portion between the first connecting curved surface 130*a* and the proximal end side portion 140*b*, and the portion between the second connecting curved surface 130*b* and the proximal end side portion 140*b*, these lines merely represent boundaries and do not represent the ridgelines formed by the surfaces intersecting each other. As described above, the first bevel surface 105*a* is smoothly connected to the proximal end side portion 140*b* via the first connecting curved surface 130*a* of the distal end side portion 140*a*, and the second bevel surface 105*b* is smoothly connected to the proximal end side portion 140*b* via the second connecting curved surface 130*b* of the distal end side portion 140*a*. In FIGS. 4A and 4D, the line drawn between the first bevel surface 105*a*/second bevel surface 105*b* and the distal end side portion 140*a* and the line drawn between the distal end side portion 140*a* and the proximal end side portion 140*b* simply represent the boundary lines similarly to the description above.

Moreover, either of the distal end side portion 140*a* and the proximal end side portion 140*b* of the third bevel surface 105*c* is inclined so as to gradually come closer to the center axis O toward the needle point 108 side in the center axis direction A, and the inclination angle of each of the distal end side portion 140*a* and the proximal end side portion 140*b* with respect to the center axis direction A is greater than the inclination angle of an outer wall of the main body portion 102 with respect to the center axis direction A in the cross section including the entire center axis O. Since each of the distal end side portion 140*a* and the proximal end side portion 140*b* is a protruding curved surface, the "inclination angle of the distal end side portion with respect to the center axis direction" as described herein corresponds to the angle formed by a tangent line at an arbitrary point on the distal end side portion of the third bevel surface and the center axis, on a cross section including the entire center axis and passing through the distal end side portion on the third bevel surface. The "inclination angle of the proximal end side portion with respect to the center axis direction" corresponds to the angle formed by a tangent line at an arbitrary point on the distal end side portion of the third bevel surface and the center axis, on a cross section including the entire center axis and passing through the proximal end side portion on the third bevel surface.

The outer diameter of the tubular member constituting the puncture needle 101 is uniform regardless of the position in the center axis direction A, and the outer wall of the tubular member extends in the center axis direction A when viewed in a cross section including the entire center axis O. Accordingly, as long as the distal end side portion 140*a* and the proximal end side portion 140*b* of the third bevel surface 105*c* are inclined with respect to the center axis direction A, the inclination angle of each of the distal end side portion 140*a* and the proximal end side portion 140*b* is greater than the inclination angle of the outer wall of the main body portion 102. In a case, however, where the tubular member constituting the puncture needle 101 is configured to have the outer diameter that gradually decreases or gradually increases toward the distal end portion 103 side in the center axis direction A, it is preferable to configure such that each of the distal end side portion 140*a* and the proximal end side portion 140*b* of the third bevel surface 105*c* is not merely inclined with respect to the center axis direction A, but also inclined with respect to the outer wall of the main body portion 102 in the cross section including the entire center axis O.

Similarly to the second blade surface portion 6 and the third blade surface portion 7 of the puncture needle 1 described above, each of the second blade surface portion 106 and the third blade surface portion 107 is constituted with a curved surface in which the angle γ with respect to the center plane X in a cross section orthogonal to the center axis direction A gradually increases toward the needle point 108 side in the center axis direction A.

The second blade surface portion 106 is formed on the back side of the first bevel surface 105*a*, and the third blade surface portion 107 is formed on the back side of the second bevel surface 105*b*. The second blade surface portion 106 and the third blade surface portion 107 intersect each other to be a ridgeline and form the blade edge 123 having the needle point 108 as one end by the ridgeline on the needle point 108 side in the center axis direction A.

Moreover, the first bevel surface 105*a* and the second blade surface portion 106 intersect each other to be a ridgeline and form a blade edge 124 having the needle point 108 as one end by the ridgeline. More specifically, the blade edge 124 is constituted with the ridgeline formed by the outer edge of the first bevel surface 105*a* and the outer edge of the second blade surface portion 106.

Furthermore, the second bevel surface 105*b* and the third blade surface portion 107 intersect each other to be a ridgeline and form a blade edge 125 having the needle point 108 as one end by the ridgeline. More specifically, the blade edge 125 is constituted with the ridgeline formed by the outer edge of the second bevel surface 105*b* and the outer edge of the third blade surface portion 107.

Hereinafter, for convenience of description, the blade edge 123 formed by the ridgeline on which the second blade surface portion 106 and the third blade surface portion 107 intersect each other will be referred to as "a first blade edge 123", the blade edge 124 formed by the ridgeline on which the first bevel surface 105*a* and the second blade surface portion 106 intersect each other will be referred to as "a second blade edge 124", the blade edge 125 formed by the ridgeline on which the second bevel surface 105*b* and the third blade surface portion 107 intersect each other will be referred to as "a third blade edge 125", and the blade edge 109 formed by the ridgeline on which the first bevel surface 105*a* and the second bevel surface 105*b* intersect each other will be referred to as "a fourth blade edge 109".

In this manner, the puncture needle 101 includes the first blade surface portion 105 as the front side blade surface and the second blade surface portion 106 and the third blade surface portion 107 as the back side blade surfaces. Accordingly, it is possible to sharpen the needle point 108 of the puncture needle 101 and reduce the penetration resistance in the vicinity of the needle point 108. With a configuration in which both the second blade surface portion 106 and the third blade surface portion 107 are constituted with curved surfaces in which the angle γ with respect to the center plane X in a cross section orthogonal to the center axis direction A gradually increases toward the needle point 108 side in the center axis direction A, it is possible to sharpen the portion in the vicinity of the needlepoint 108 and facilitate achieving a configuration that is unlikely to form a ridgeline (junction) having a possibility of becoming the penetration resistance between the second blade surface portion 106/third blade surface portion 107 and the outer circumferential surface of the tubular member constituting the puncture needle 101.

Examples of materials applicable as the puncture needle 101 a metal material such as stainless steel, aluminum or an aluminum alloy, titanium or a titanium alloy.

Hereinafter, the shape of the blade surface 104 according to the present embodiment will be described in detail with reference to FIGS. 6A-6F.

FIG. 6A illustrates a cross section taken along line VI-VI in FIGS. 5A and 5B, that is, a cross section passing through the proximal end side portion 140*b* of the third bevel surface 105*c* and orthogonal to the center axis direction A. As illustrated in FIG. 6A, an angle θ1 of the proximal end side portion 140*b* with respect to the center plane X in cross section VI-VI in FIGS. 5A and 5B is about 90 degrees, and the angle θ of the proximal end side portion 140*b* with respect to the center plane X is about 90 degrees regardless of the position in the center axis direction A, namely, any position other than on cross section VI-VI in FIGS. 5A and 5B. In other words, as illustrated in FIG. 6A, the proximal end side portion 140*b* on the third bevel surface 105*c* extends linearly in a direction orthogonal to the center plane X in the cross section orthogonal to the center axis direction A.

FIG. 6B illustrates a cross section taken along line VII-VII in FIGS. 5A and 5B, that is, a cross section passing through the distal end side portion 140*a* of the third bevel surface 105*c* and orthogonal to the center axis direction A. As illustrated in FIG. 6B, an angle θ2 of the distal end side portion 140*a* with respect to the center plane X in cross section VII-VII in FIGS. 5A and 5B is about 90 degrees, and the angle θ of the distal end side portion 140*a* with respect to the center plane X is about 90 degrees regardless of the position in the center axis direction A, namely, any position other than on cross section VII-VII in FIGS. 5A and 5B. In other words, as illustrated in FIG. 6B, the distal end side portion 140*a* on the third bevel surface 105*c* extends linearly in a direction orthogonal to the center plane X in the cross section orthogonal to the center axis direction A. Note that in FIG. 6B and FIGS. 6C to 6F to be referred to below, the boundary line between the distal end side portion 140*a* and the proximal end side portion 140*b* on the third bevel surface 105*c* is indicated by a two-dot chain line.

FIG. 6C is a cross section taken along line VIII-VIII in FIGS. 5A and 5B, that is, a cross section orthogonal to the center axis direction A at a position where the first bevel surface 105*a* and the second bevel surface 105*b* are connected to the distal end side portion 140*a* of the third bevel surface 105*c*. As illustrated in FIG. 6C, an angle θ3 of each of the first bevel surface 105*a* and the second bevel surface 105*b* with respect to the center plane X in cross section VIII-VIII in FIG. 5 is about 90 degrees, linearly extending in a direction orthogonal to the center plane X as illustrated in FIG. 6C. In other words, the first bevel surface 105*a* and the second bevel surface 105*b* are smoothly connected to each other without forming ridgelines with the distal end side portion 140*a*.

FIG. 6D is a cross sectional view taken along line IX-IX in FIGS. 5A and 5B, that is, a cross section orthogonal to the center axis direction A at a position where the first bevel surface 105a and the second bevel surface 105b are formed in the center axis direction A and at the same time, at a position where the second blade surface portion 106 and the third blade surface portion 107 are not formed. As illustrated in FIG. 6D, an angle θ4 of each of the first bevel surface 105a and the second bevel surface 105b with respect to the center plane X in cross section IX-IX in FIGS. 5A and 5B is an acute angle smaller than the angle θ3. Note that in FIG. 6D and in FIGS. 6E and 6F to be referred to below, the boundary line between the first bevel surface 105a/second bevel surface 105b and the distal end side portion 140a of the third bevel surface 105c is indicated by a two-dot chain line.

FIG. 6E is a cross sectional view taken along line X-X in FIGS. 5A and 5B, that is, a cross section orthogonal to the center axis direction A at a position where the first bevel surface 105a, the second bevel surface 105b, the second blade surface portion 106, and the third blade surface portion 107 are formed in the center axis direction A and at the same time, at a position where the opening 111 exists in the center axis direction A. In other words, FIG. 6E is a cross section orthogonal to the center axis direction A at a position where the first blade edge 123 and the fourth blade edge 109 are not formed in the center axis direction A and at the same time, at a position where the second blade edge 124 and the third blade edge 125 are formed. As illustrated in FIG. 6E, an angle θ5 of each of the first bevel surface 105a and the second bevel surface 105b in cross section X-X in FIGS. 5A and 5B with respect to the center plane X is an acute angle smaller than the angle θ3 and smaller than the angle θ4.

Moreover, as illustrated in FIG. 6E, the second blade surface portion 106 and the third blade surface portion 107 are formed in cross section X-X in FIGS. 5A and 5B, and each of the second blade surface portion 106 and the third blade surface portion 107 extends linearly at a predetermined acute angle γ5 with respect to the center plane X in a cross sectional view of FIG. 6E.

FIG. 6F illustrates a cross section taken along line XI-XI in FIGS. 5A and 5B, that is, a cross section orthogonal to the center axis direction A at a position where the first blade edge 123, the second blade edge 124, the third blade edge 125, and the fourth blade edge 109 are formed. As illustrated in FIG. 6F, an angle θ6 of each of the first bevel surface 105a and the second bevel surface 105b in cross section XI-XI in FIGS. 5A and 5B with respect to the center plane X is an acute angle smaller than the angle θ3, smaller than the angle θ4, and smaller than the angle θ5.

Moreover, as illustrated in FIG. 6F, an angle γ6 of each of the second blade surface portion 106 and the third blade surface portion 107 with respect to the center plane X in cross section XI-XI in FIGS. 5A and 5B is an acute angle greater than the angle γ5.

In this manner, the first bevel surface 105a and the second bevel surface 105b are straight lines in a cross sectional view orthogonal to the center axis direction A, and the angle θ with respect to the center plane X in the cross section orthogonal to the center axis direction A gradually decreases toward the needle point 108 side (in a closer position to the needle point 108) in the center axis direction A (refer to FIGS. 6C to 6F). Moreover, the second blade surface portion 106 and the third blade surface portion 107 are straight lines in a cross sectional view orthogonal to the center axis direction A, and the angle γ with respect to the center plane X in the cross section orthogonal to the center axis direction A gradually increases toward the needle point 108 side (in a closer position to the needle point 108) in the center axis direction A (refer to FIGS. 6E and 6F).

Note that while FIGS. 6C to 6F illustrate the angles θ3 to θ6 of the second bevel surface 105b with respect to the center plane X respectively, the angles of the first bevel surface 105a with respect to the center plane X are also the same as the angles θ3 to θ6 of the second bevel surface 105b. Note that while FIGS. 6E and 6F illustrate the angles γ5 and γ6 of the third blade surface portion 107 with respect to the center plane X respectively, the angles of the second blade surface portion 106 with respect to the center plane X are also the same as the angles γ5 and γ6 of the third blade surface portion 107. Furthermore, the four cross sections in FIGS. 6C to 6F are merely examples to illustrate the size relationship between the angles θ3 to θ6 and the size relationship between the angles γ5 and γ6, and the size relationship of the above-described angles θ and γ is not limited to these four cross sections.

While the puncture needle 101 is configured such that both the second blade surface portion 106 and the third blade surface portion 107 are constituted with curved surfaces in which the angle γ with respect to the center plane X in a cross section orthogonal to the center axis direction A gradually increases toward the needle point 108 side in the center axis direction A, it is also allowable to configure such that any one of the second blade surface portion 106 and the third blade surface portion 107 is constituted with such a curved surface while the other is constituted with a plane or a curved surface having another surface shape.

Note that the puncture needle according to the present invention is achievable by various configurations and is not limited to the configurations of the above-described embodiments. Rather, the puncture needle can be modified but remain within the scope and spirit of the invention.

Second Embodiment

Finally, a method for manufacturing a puncture needle 1 according to an embodiment of the present invention will be described. FIG. 8 is a flowchart illustrating a method for manufacturing the puncture needle 1 according to the present embodiment. As illustrated in FIG. 8, a method for manufacturing the puncture needle 1 includes a tubular member acquisition step S1 of obtaining a tubular member as a hollow rod-like member among the rod-like member, being a state before edge formation of the puncture needle 1, and includes a blade surface forming step S2 of forming the puncture needle 1 by forming the blade surface 4 (refer to FIGS. 1, 2, or the like) on at least one end portion of the tubular member. The method for manufacturing the puncture needle 1 according to the present embodiment further includes a polishing step S3 of polishing the formed puncture needle 1 using various types of polishing treatment such as electrolytic polishing treatment after the blade surface forming step S2.

The tubular member acquisition step S1 can be performed by various known methods and includes: for example, a reception step S1-1 of receiving a band-shaped metallic plate material into a press molding machine; a press molding step S1-2 of obtaining a plurality of pipe bodies partially connected to the plate material successively press molded by the press molding machine; a joining step S1-3 of joining the joints of the pipe bodies with welding or an adhesive; a straightening step S1-4 of straightening the shape of the pipe body such that the center axis of the pipe body is substantially a straight line, and a separation step S1-5 of obtaining the tubular member in a state before edge formation of the puncture needle 101 by separating the pipe body from the plate material.

Figure 9A:
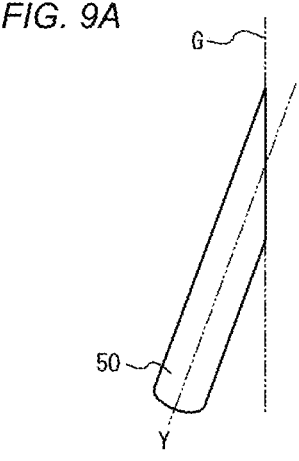
Figure 9B:
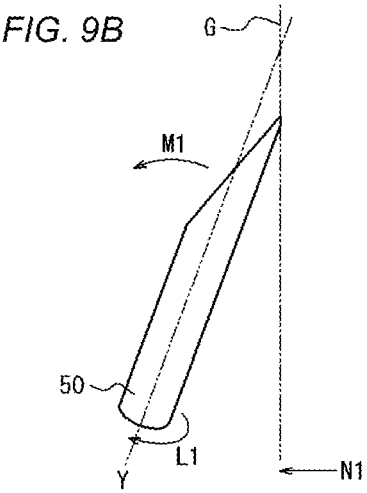
Figure 9C:
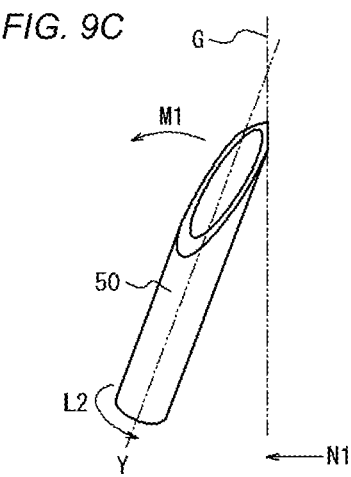

The blade surface forming step S2 includes a first blade surface portion forming step S2-1 of forming the first blade surface portion 5 (refer to FIGS. 1, 2, or the like), a third blade surface portion forming step S2-2 of forming the third blade surface portion 7 (refer to FIGS. 1, 2, or the like), and a second blade surface portion forming step S2-3 of forming the second blade surface portion 6 (refer to FIGS. 1, 2, or the like). FIGS. 9A-9C are general views illustrating an outline of a method for forming the first to third blade surface portions 5 to 7 in the blade surface forming step S2, in which FIG. 9A illustrates a method for forming the first blade surface portion 5 in the first blade surface portion forming step S2-1, FIG. 9B illustrates a method for forming the third blade surface portion 7 in the third blade surface portion forming step S2-2, and FIG. 9C illustrates a method for forming the second blade surface portion 6 in the second blade surface portion forming step S2-3.

As illustrated in FIG. 9A, the first blade surface portion forming step S2-1 forms the first blade surface portion 5 at the end portion of a tubular member 50 by grinding processing with a grindstone. The first blade surface portion forming step S2-1 of the present embodiment is performed without causing the tubular member 50 to pivot, and without varying the tilt angle of a center axis Y of the tubular member 50 with respect to the grinding surface of the grindstone. Alternatively, this first blade surface portion 5 can also be formed in the above-described press molding step S1-2 in the tubular member acquisition step S1. Moreover, the first blade surface portion 5 can be formed by wire cutting, or the like, instead of the grinding processing with a grindstone. In FIGS. 9A to 9C, the grinding surface of the rotating grindstone is represented by a two-dot chain line "G".

As illustrated in FIGS. 9B and 9C, the third blade surface portion forming step S2-2 and the second blade surface portion forming step S2-3 form the third blade surface portion 7 and the second blade surface portion 6 by grinding by bringing the tubular member 50 obtained in the tubular member acquisition step S1 into sliding contact with a grinding surface G of the grindstone while moving the grindstone rotating in a high speed (plunge oscillation grinding).

Specifically, the third blade surface portion forming step S2-2 and the second blade surface portion forming step S2-3 forms the third blade surface portion 7 and the second blade surface portion 6 as blade surface portions constituted with curved surfaces by bringing the back side of the first blade surface portion 5 into sliding contact with the grinding surface G of the grindstone while varying the tilt angle of the center axis Y of the tubular member 50 with respect to the grinding surface G of the grindstone while causing the tubular member 50 to pivot about the center axis Y of the tubular member 50. Note that the third blade surface portion forming step S2-2 and the second blade surface portion forming step S2-3 move the grindstone to be closer to the tubular member 50 so as to maintain the sliding contact state between the grinding surface G of the grindstone and the back side of the first blade surface portion 5 even with pivoting and variation in the inclination angle of the tubular member 50 (refer to the arrow "N1" in FIGS. 9B and 9C).

More specifically, the third blade surface portion forming step S2-2 can be executed by bringing the back side of the first blade surface portion 5 into sliding contact with the grinding surface G of the grindstone while varying the tilt angle of the center axis Y of the tubular member 50 with respect to the grinding surface G of the grindstone in one tilt direction (refer to the arrow "M1" in FIG. 9B) while causing the tubular member 50 to pivot in one direction (refer to the arrow "L1" in FIG. 9B) about the center axis Y of the tubular member 50. The third blade surface portion forming step S2-2 forms the third blade surface portion 7 and the third blade edge 16. While in the third blade surface portion forming step S2-2, the pivoting speed and the tilting speed of the tubular member 50 can be fixed or varied in accordance with the grinding position, it is preferable to fix the speeds so as not to form a ridgeline (junction) having a possibility of becoming the penetration resistance.

After the third blade surface portion forming step S2-2, the tubular member 50 is re-set to the position and posture suitable for starting the second blade surface portion forming step S2-3, and after completion of the re-setting, the second blade surface portion forming step S2-3 can be started.

The second blade surface portion forming step S2-3 can be executed by bringing the position on the back side of the first blade surface portion 5 and adjacent to the third blade surface portion 7 in a circumferential direction into sliding contact with the grinding surface G of the grindstone while varying the tilt angle of the center axis Y of the tubular member 50 with respect to the grinding surface G of the grindstone in the same direction of the one tilt direction at the third blade surface portion forming step S2-2 (refer to the arrow "M1" in FIG. 9C) while causing the tubular member 50 to pivot in the direction opposite to the one direction at the third blade surface portion forming step S2-2 (refer to the arrow "L2" in FIG. 9C) about the center axis Y of the tubular member 50. The second blade surface portion forming step S2-3 forms the second blade surface portion 6, the first blade edge 23, and the second blade edge 15. Similarly to the above-described third blade surface portion forming step S2-2, while the pivoting speed and the tilting speed of the tubular member 50 can be fixed or varied in accordance with the grinding position, in the second blade surface portion forming step S2-3, it is preferable to fix the speeds so as not to form a ridgeline (junction) having a possibility of becoming the penetration resistance.

In this manner, in the blade surface forming step S2 in the method for manufacturing the puncture needle 1 according to the present embodiment, more specifically, in the third blade surface portion forming step S2-2 and the second blade surface portion forming step S2-3, it is possible to form the third blade surface portion 7 and the second blade surface portion 6 each being constituted with a curved surface by bringing the end portion of the tubular member 50 into sliding contact with the grinding surface G of the grindstone while rotating the grindstone, moving the grindstone, causing the tubular member 50 to pivot, and varying the tilt angle of the tubular member 50 at the same time.

Moreover, the puncture needle 151 illustrated in FIGS. 10A-10D can be configured such that one end portion on which the blade surface 154 is formed has a substantially elliptical cross sectional outline by applying press-work onto the one end portion of the cylindrical tubular member in the tubular member acquisition step S1 or immediately before the first blade surface portion forming step S2-1. The subsequent steps are similar to those described above. The puncture needle 1' illustrated in FIG. 7 can be configured such that a solid rod-like member is formed by a known solid rod-like member acquisition step of forming a solid rod-like member instead of the above-described tubular member acquisition step S1, and that the blade surface 4' is formed on one end portion of the solid rod-like member with a method similar to the above-described blade surface forming step S2.

REFERENCE NUMERAL LIST 1, 1', 101, 151 Puncture needle
2, 2', 102, 152 Main body portion
3, 103, 153 Distal end portion
4, 4', 104, 154 Blade surface
5, 5', 105, 155 First blade surface portion
6, 106, 156 Second blade surface portion
7, 107, 157 Third blade surface portion
8, 108, 158 Needle point
10, 110, 160 Hollow portion
11, 111 Opening
13 Inner edge of first blade surface portion
14 Outer edge of first blade surface portion
15 Blade edge (second blade edge)
16 Blade edge (third blade edge)
17 Main body portion side outer edge portion
23, 123, 173 Blade edge (first blade edge)
50 Tubular member (rod-like member)
105a First bevel surface
105b Second bevel surface
105c Third bevel surface
109 Blade edge (fourth blade edge)
124 Blade edge (second blade edge)
125 Blade edge (third blade edge)
130a First connecting curved surface
130b Second connecting curved surface
140a Distal end side portion
140b Proximal end side portion
A Center axis direction
G Grinding surface of grindstone
L1, L2 Pivoting direction of tubular member
M1 Tilt direction of tubular member
N1 Moving direction of grindstone
Y Center axis of tubular member
O Center axis
P, Q Terminal point of blade edge
R1 Major axis
R2 Minor axis
S1, S2 Width of main body distal end portion
X Center plane
W1, W2 Cutting width of blade edge
BL Outer circumference of main body barrel portion
α Blade tip angle
β1, β2 Center angle of extension range of blade edge
θ Angle of first blade surface portion with respect to center plane in cross section orthogonal to center axis direction
γ Angles of second and third blade surface portions with respect to center plane in cross section orthogonal to center axis direction
τ: intersecting angle

What is claimed is:

1. A medical puncture needle comprising:
a distal end portion including a needle point; and
a rod-like main body portion continuous with the distal end portion,
wherein:
the distal end portion includes a blade surface, the blade surface comprises:
a first blade surface portion on a front side of the distal end portion, the first blade surface portion being inclined with respect to a center axis of the main body portion and extending to the needle point, and
a second blade surface portion on a back side of the distal end portion, and
when a virtual plane including the center axis of the main body portion is established, the second blade surface portion comprises a curved surface in which, in each of a plurality of cross-sections orthogonal to the center axis direction, there is an angle between the curved surface and the virtual plane, and said angles gradually increase toward a needle point side in the center axis direction.

2. The medical puncture needle according to claim 1, wherein:
the blade surface comprises a third blade surface portion on the back side of the distal end portion, and
the second blade surface portion and the third blade surface portion intersect at a ridgeline that forms a blade edge having the needle point at one end.

3. The medical puncture needle according to claim 2, wherein the third blade surface portion comprises a curved surface in which, in each of the plurality of cross-sections orthogonal to the center axis direction, there is an angle between the curved surface and the virtual plane, and said angles gradually increase toward the needle point side in the center axis direction.

4. The medical puncture needle according to claim 1, wherein the virtual plane is in a plane perpendicular to the first blade surface portion.

5. A medical puncture needle comprising:
a distal end portion including a needle point; and
a rod-like main body portion continuous with the distal end portion,
wherein:
the distal end portion includes a blade surface,
the blade surface comprises:
a first blade surface portion on a front side of the distal end portion, the first blade surface portion being inclined with respect to a center axis of the main body portion and extending to the needle point,
a second blade surface portion on a back side of the distal end portion, and
a third blade surface portion on the back side of the distal end portion,
the second blade surface portion and the third blade surface portion intersect at a first ridgeline that forms a first blade edge having the needle point at one end,
the first blade surface portion and the second blade surface portion intersect at a second ridgeline that forms a second blade edge having the needle point at one end,
the first blade surface portion and the third blade surface portion intersect at a third ridgeline that forms a third blade edge having the needle point at one end, and
the second blade edge is curved, and the third blade edge is curved.

6. The medical puncture needle according to claim 5, wherein an outer edge of the first blade surface portion is formed of the second blade edge, the third blade edge, and a protruding curved line-shaped main body portion side outer edge portion connecting an end of the second blade edge on the main body portion side to an end of the third blade edge on the main body portion side.

7. The medical puncture needle according to claim 6, wherein the second blade edge and the third blade edge are connected to the main body portion side outer edge portion along a continuous curved line that does not form an apex.

* * * * *